(12) United States Patent
Lenker et al.

(10) Patent No.: US 11,911,066 B2
(45) Date of Patent: *Feb. 27, 2024

(54) ENDOLUMINAL PUNCH SYSTEM WITH ENERGY

(71) Applicant: Indian Wells Medical, Inc., Lake Forest, CA (US)

(72) Inventors: Jay A. Lenker, Lake Forest, CA (US); James A. Carroll, Long Beach, CA (US); Peter van der Sluis, Palm Springs, CA (US); Eugene M. Breznock, Winters, CA (US)

(73) Assignee: Indian Wells Medical, Inc., Lake Forest, CA (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/590,640

(22) Filed: Feb. 1, 2022

(65) Prior Publication Data
US 2022/0151655 A1    May 19, 2022

Related U.S. Application Data

(63) Continuation of application No. 17/445,042, filed on Aug. 13, 2021, now Pat. No. 11,234,728, which is a
(Continued)

(51) Int. Cl.
*A61B 17/3207* (2006.01)
*A61M 29/00* (2006.01)
(Continued)

(52) U.S. Cl.
CPC ............. *A61B 17/320783* (2013.01); *A61B 17/32053* (2013.01); *A61M 29/00* (2013.01);
(Continued)

(58) Field of Classification Search
CPC ...... A61B 17/320783; A61B 17/32053; A61B 2017/00867; A61B 2090/3966;
(Continued)

(56) References Cited

U.S. PATENT DOCUMENTS 5,421,819 A   6/1995 Edwards et al.
5,924,424 A   7/1999 Stevens et al.
(Continued)

OTHER PUBLICATIONS

International Search Report and Written Opinion dated Jun. 23, 2021 from IA PCT/US2021/020309.

*Primary Examiner* — Julian W Woo
(74) *Attorney, Agent, or Firm* — Crockett & Crockett, PC; K. David Crockett, Esq.

(57) ABSTRACT

An endoluminal punch system including a sheath and dilator. The endoluminal punch may include energy delivery system capable of being transmitted from the proximal end to the distal end of the endoluminal punch to assist with tissue crossing and incisions. The dilator may include selectively deployable cutting mechanism to create incisions in tissue that are larger than their basic external diameter. The system may also be configured to reduce the risk of generating plastic emboli during insertion of the endoluminal punch.

12 Claims, 16 Drawing Sheets

Related U.S. Application Data continuation of application No. 15/930,918, filed on May 13, 2020, now Pat. No. 11,090,080.

(60) Provisional application No. 62/983,008, filed on Feb. 28, 2020, provisional application No. 62/877,159, filed on Jul. 22, 2019, provisional application No. 62/848,450, filed on May 15, 2019.

(51) Int. Cl.
  *A61B 17/3205* (2006.01)
  *A61B 90/00* (2016.01)
  *A61B 17/00* (2006.01)

(52) U.S. Cl.
  CPC ............... *A61B 2017/00247* (2013.01); *A61B 2017/00867* (2013.01); *A61B 2017/320791* (2013.01); *A61B 2090/066* (2016.02); *A61B 2090/3966* (2016.02)

(58) Field of Classification Search
  CPC .. A61B 2090/066; A61B 2017/320791; A61B 2017/00247; A61M 29/00
  See application file for complete search history.

(56) References Cited

U.S. PATENT DOCUMENTS

| | | | |
|---|---|---|---|
| 6,132,438 | A | 10/2000 | Fleischman et al. |
| 7,666,203 | B2 | 2/2010 | Chanduszko et al. |
| 8,096,959 | B2 * | 1/2012 | Stewart ............ A61B 17/00234 |
| | | | 607/128 |
| 8,540,674 | B2 | 9/2013 | Kassab et al. |
| 8,663,243 | B2 | 3/2014 | Lamson et al. |
| 9,821,145 | B2 | 11/2017 | Kurth et al. |
| 10,993,735 | B2 | 5/2021 | Vardi et al. |
| 11,020,173 | B2 * | 6/2021 | Davies ............... A61B 18/1477 |
| 11,090,080 | B2 | 8/2021 | Lenker et al. |
| 11,234,728 | B2 * | 2/2022 | Lenker ............... A61B 17/3478 |
| 2010/0228276 | A1 | 9/2010 | Breznock |
| 2020/0367924 | A1 | 11/2020 | Lenker et al. |

\* cited by examiner

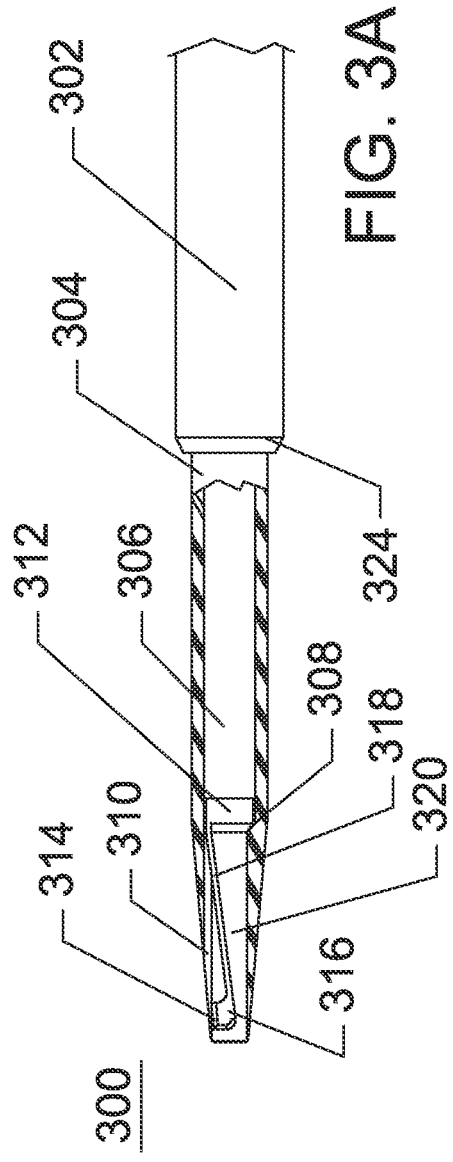
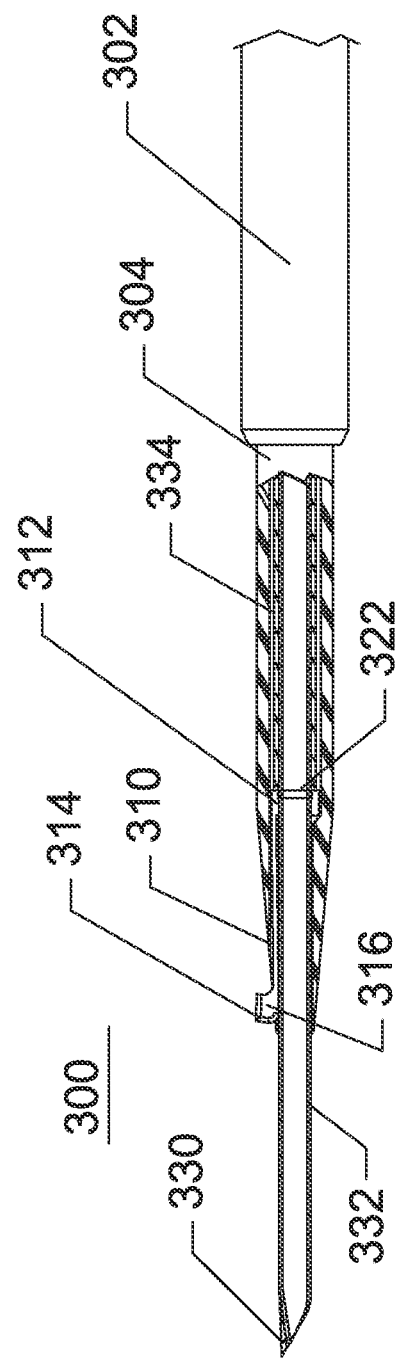

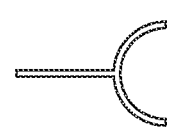 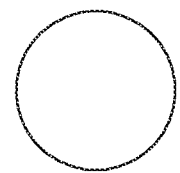
FIG. 5C
 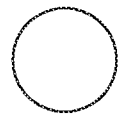
FIG. 5B
 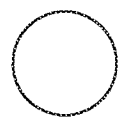
FIG. 5A

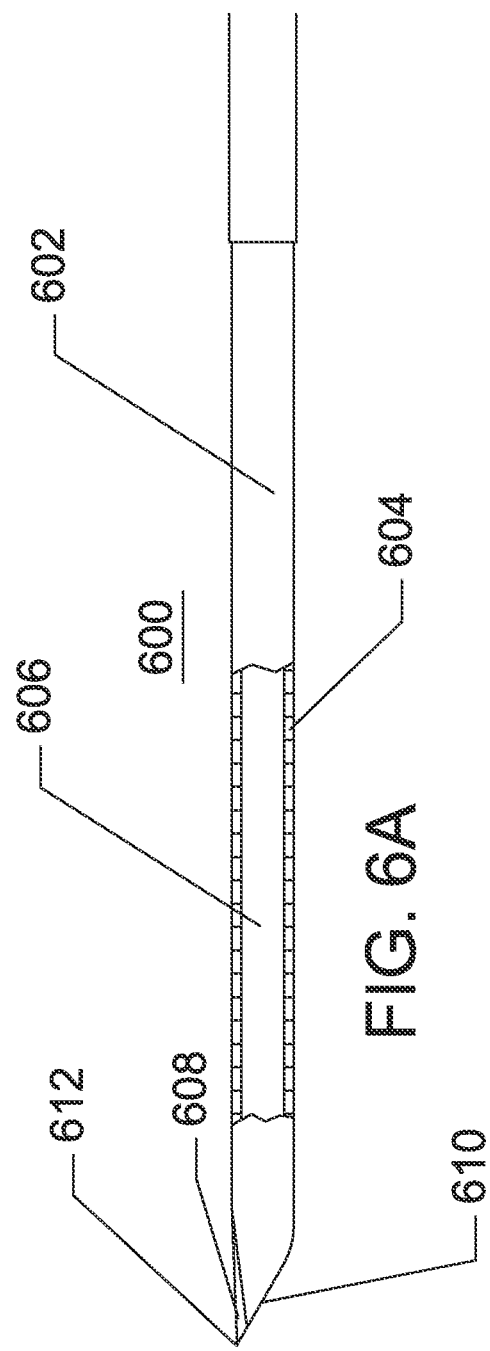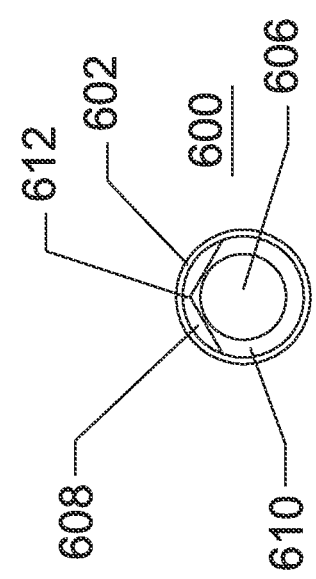
FIG. 6A
FIG. 6B

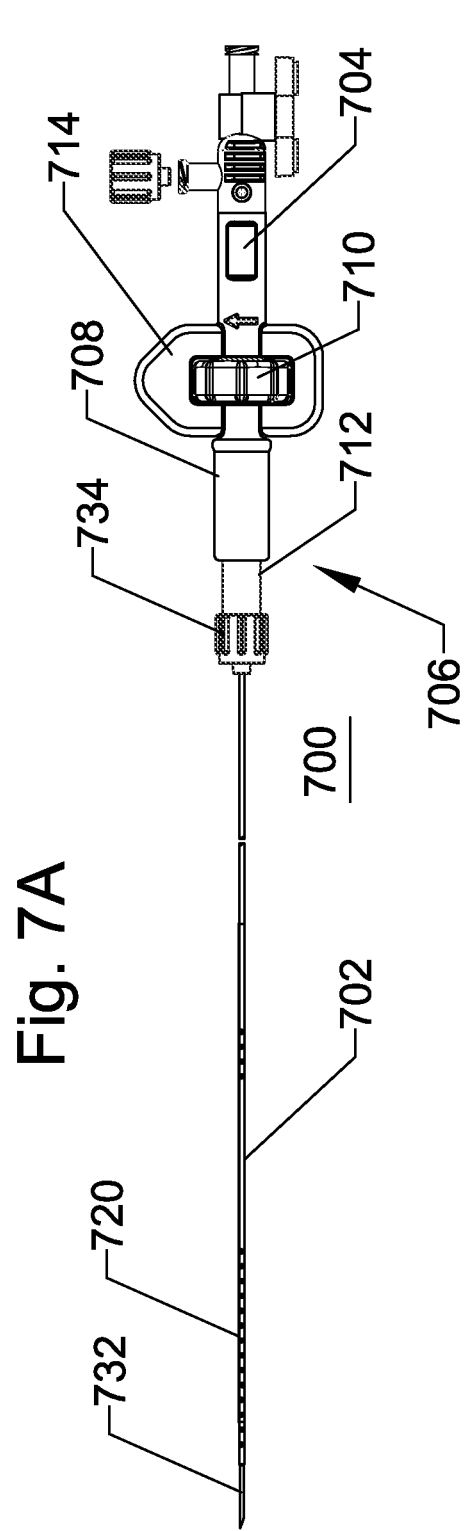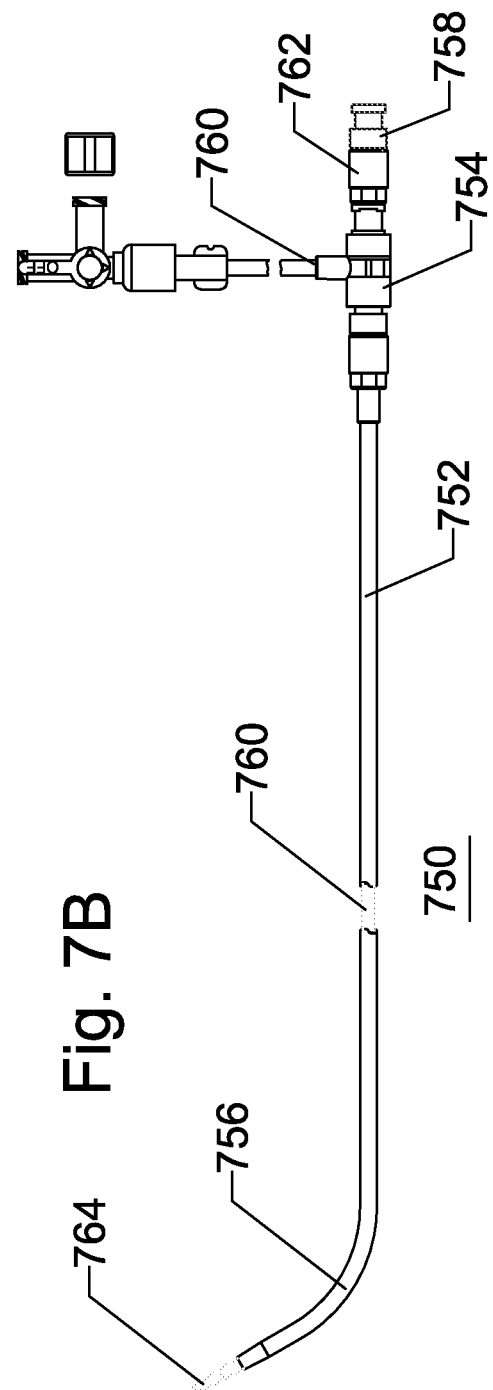

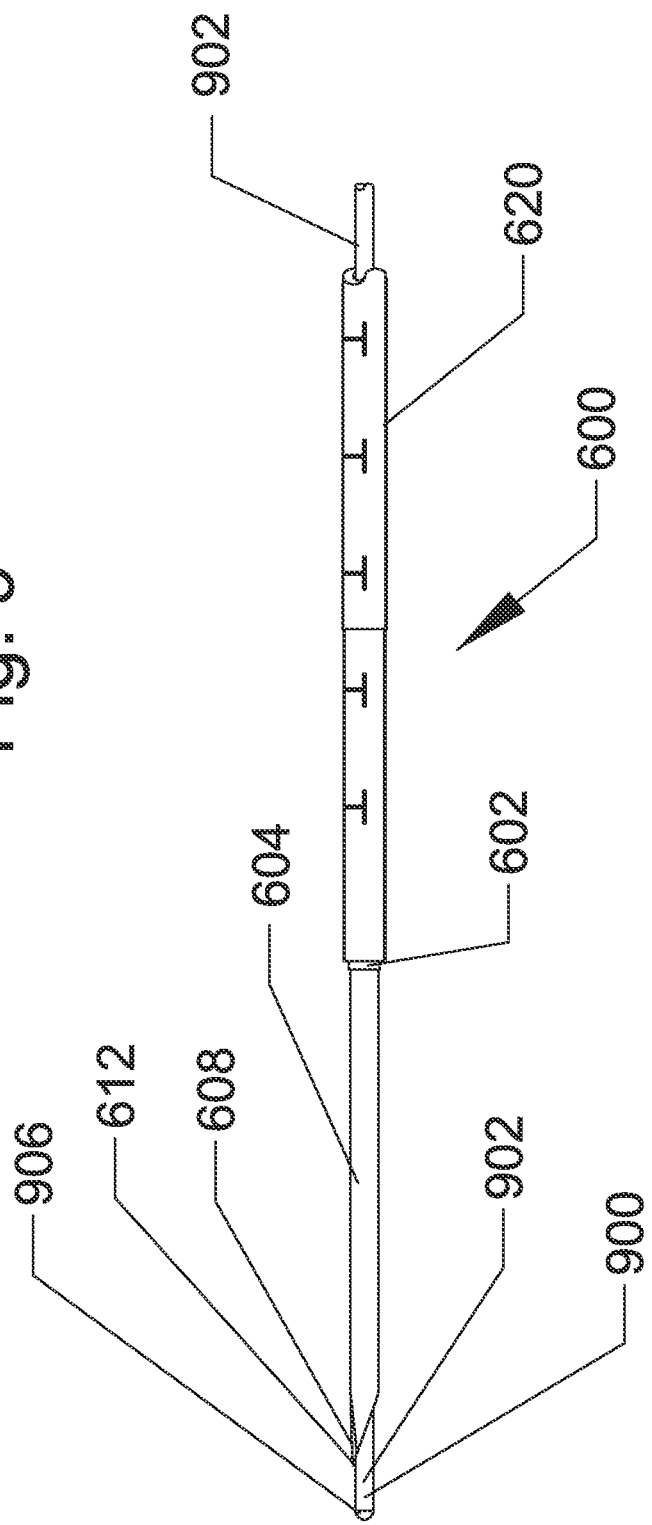

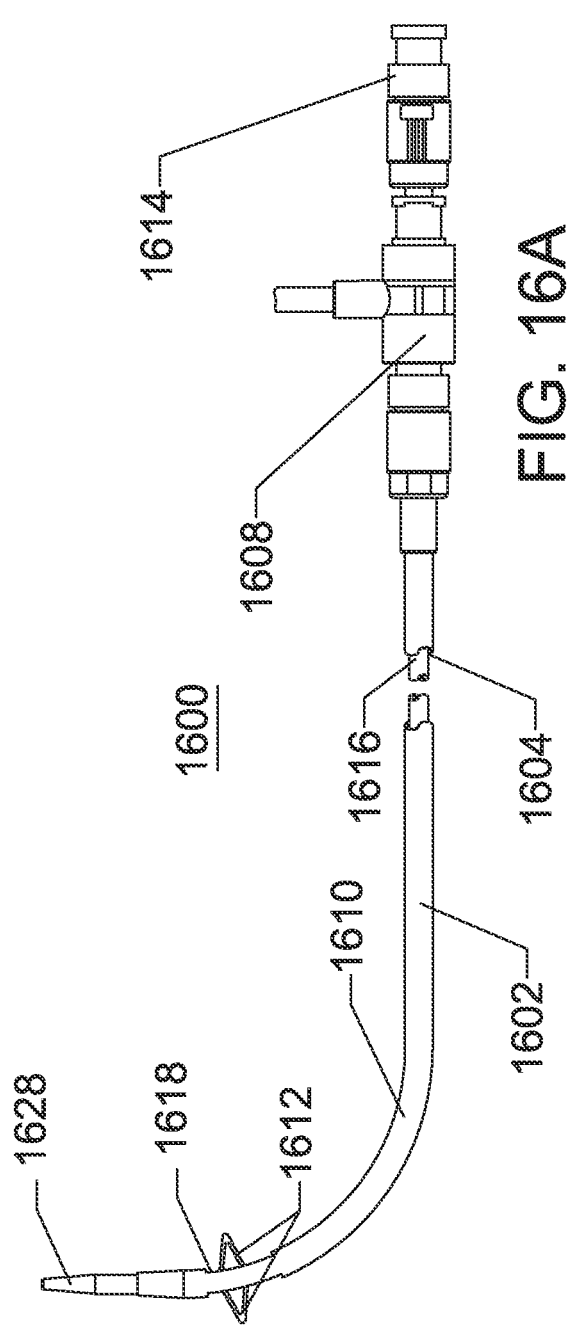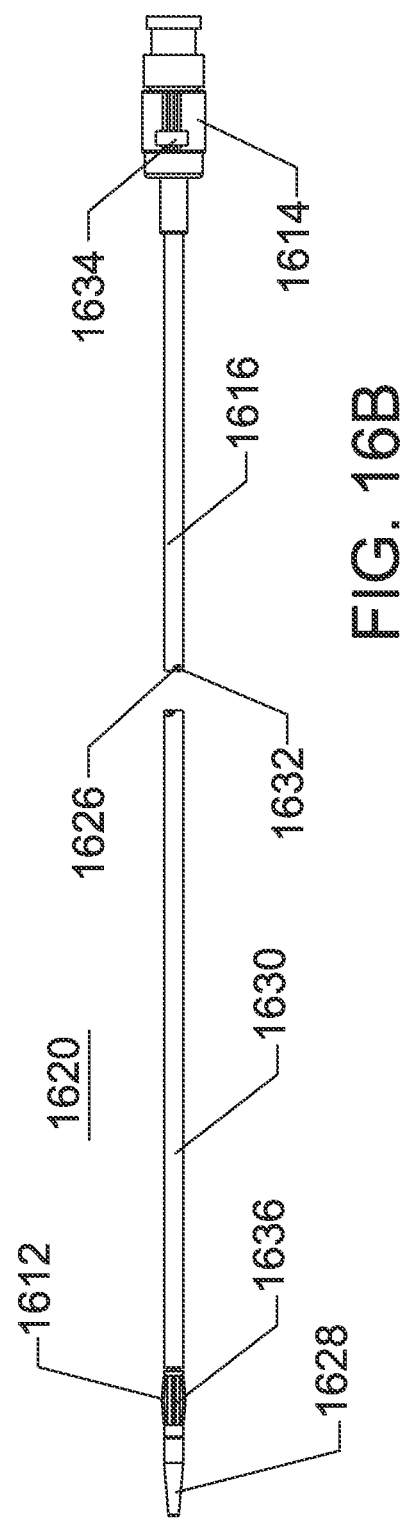

ENDOLUMINAL PUNCH SYSTEM WITH ENERGY

This application is a continuation of U.S. application Ser. No. 17/445,042, filed Aug. 13, 2021, now U.S. Pat. No. 11,234,728, which is a continuation of U.S. application Ser. No. 15/930,918, filed May 13, 2020, now U.S. Pat. No. 11,090,080, which claims priority to U.S. Provisional Application 62/848,450, filed May 15, 2019, U.S. Provisional Application 62/877,159, filed Jul. 22, 2019, and U.S. Provisional Application 62/983,008, filed Feb. 28, 2020.

FIELD OF THE INVENTION

The inventions described below relate to the field of endoluminal punches.

BACKGROUND

The currently accepted procedure for left atrial access involves routing a needle called a Brockenbrough needle into the right atrium with the Brockenbrough needle pre-placed within a guiding catheter. The guiding catheter specifically developed for use with a Brockenbrough needle is called a Mullins catheter or transseptal introducer. Other transseptal introducers are now available with features not present on the Mullins transseptal introducer but are essentially the same devices. The Brockenbrough needle is a long, small diameter endoluminal punch, generally formed from a first, larger diameter stainless steel tube with a second, smaller diameter stainless steel tube projecting out the distal end of the first stainless steel tube. A hub is affixed to the proximal end of the larger diameter stainless steel tube. Other devices, designed for the same purpose, can employ radiofrequency ablation to perforate the atrial wall but these devices expose the myocardium to burning, potentially reduced healing characteristics, thromboembolic events, and increased risk of subsequent scarring.

SUMMARY OF THE INVENTIONS

The endoluminal punch can be placed through an introducer, which generally comprises an outer sheath tube and an inner sheath dilator or obturator. The obturator/dilator is generally tapered at its distal tip to dilate tissue as the introducer is advanced distally.

In an embodiment, the introducer can comprise a curve at its distal end, and the punch can be a steerable endoluminal punch. The outer sheath distal end can comprise the curve as well as the dilator distal end. In other embodiments, the outer sheath can comprise the curvature while the dilator/obturator can comprise a generally straight, unbent distal end. This straight unbent distal end of the dilator can facilitate passage of the endoluminal punch with little or no risk of skiving plastic off the interior walls of the dilator lumen. The dilator (and sheath) can then be articulated by the steerable endoluminal punch. After removal of the steerable endoluminal punch and the dilator, the sheath can assume its native curvature, which can be configured for optimal access to a target region in the patient.

In other embodiments, an endoluminal punch (steerable or non-steerable) can comprise active energy delivery which causes lateral oscillatory, linear or axial hammering, or rotary motion at the distal tip to facilitate tissue penetration. This energy delivery can be transmitted from a driver at the proximal end or it can be generated by a driver affixed at or near the distal end of the steerable endoluminal punch.

In some embodiments, the steerable endoluminal punch can comprise measuring capability to provide feedback to the user or a computer regarding parameters such as, but not limited to, tip deflection angle, tip deflection percentage, axial location, ultrasound imaging (both 2-D and 3-D static as well as real-time 3-D), and the like. The steerable endoluminal punch can comprise a gauge or readout for the deflection data or it can be operationally coupled to a computer which can analyze deflection, position, and the like. Deflection sensors can include a mechanical linkage to the jackscrew or other moving part within the hub, strain gauges affixed to a portion of the bending region of the needle tubing, hall effect sensors to measure knob rotation count, and the like.

BRIEF DESCRIPTION OF THE DRAWINGS

FIG. 3A illustrates an introducer further comprising a dilator, wherein the dilator comprises a cutting element shown in its retracted configuration within the main lumen.

FIG. 3B illustrates the introducer of FIG. 3A wherein an endoluminal punch, steerable or otherwise, has been inserted through the main lumen of the dilator causing the cutting element to be forced out of the central lumen so as to project laterally outside the tapered tip of the dilator.

FIG. 4 illustrates an introducer, further comprising a dilator in side partial breakaway view, whereby the dilator comprises a central lumen and a side lumen for passage of instrumentation, linkages, and the like.

FIG. 5A upper illustrates a hole poked through a piece of tissue and FIG. 5A bottom illustrates that same hole dilated to 0.032 diameter by the tip diameter of a steerable endoluminal punch.

FIG. 5B upper illustrates a semicircular slot cut through a piece of tissue by an endoluminal punch with circumferential blade and FIG. 5B bottom shows the same semicircular slot dilated to its maximum potential diameter with no tissue stretching.

FIG. 5C upper illustrates a semicircular slot cut through a piece of tissue and an additional slit created by the cutting element of an introducer dilator as illustrated in FIG. 3B while FIG. 5C bottom shows the same slot dilated to its maximum circular diameter with no tissue stretching.

FIG. 6A illustrates a side view of a tip of an endoluminal punch configured to cut a semicircular slot through tissue.

FIG. 6B illustrates a front view of a tip of an endoluminal punch configured to cut a semicircular slot through tissue.

FIG. 7A illustrates a side view of an endoluminal punch hub including a component which connects the endoluminal punch hub to the hub of an introducer dilator, wherein the endoluminal punch is spring biased proximally away from the introducer dilator hub.

FIG. 7B illustrates a side view of an introducer sheath including a tapered dilator with a lumen capable of accepting the endoluminal punch of FIG. 7A.

FIG. 9 illustrates a side view of the distal end of the endoluminal punch wherein a blunt, protective stylet has been advanced through the lumen and protrudes out the distal end to shield the sharp tip from the wall of an introducer dilator.

FIG. 16A illustrates an introducer comprising a sheath and dilator wherein the sheath includes distal windows and the dilator includes features which radially expand through the windows in the sheath to form a motion stop.

FIG. 16B illustrates the dilator for the introducer set of FIG. 16A wherein the radially expandable features proximate the distal end are retracted radially inward.

DETAILED DESCRIPTION

Figure 1:
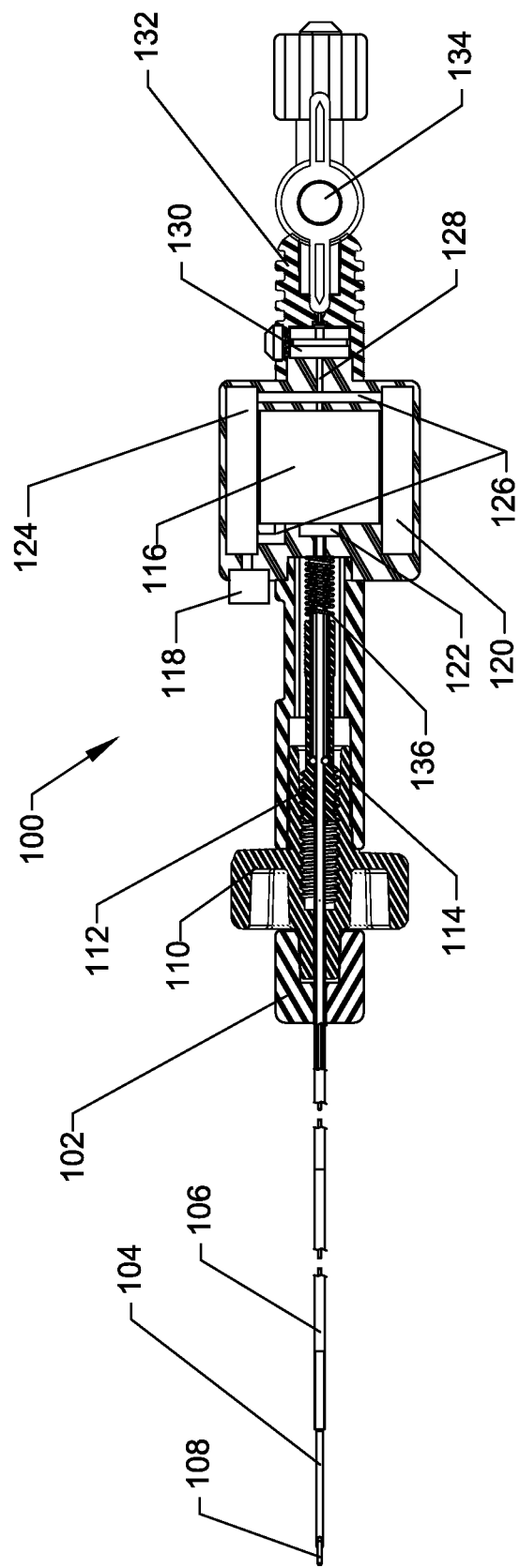
FIG. 1 illustrates a steerable endoluminal punch, as viewed from the side in cross-section, whereby the steerable endoluminal punch comprises a vibratory actuator operably connecting the primary hub structure to the jackscrew holding portion of the hub.

In accordance with current terminology pertaining to medical devices, the proximal direction will be that direction on the device that is furthest from the patient and closest to the user, while the distal direction is that direction closest to the patient and furthest from the user. These directions are applied along the longitudinal axis of the device, which is generally an axially elongate structure having one or more lumens or channels extending through the proximal end to the distal end and running substantially the entire length of the device.

In an embodiment, the invention is an endoluminally, transvascularly, or endovascularly placed tissue punch, with internal steerability, otherwise known as deflectability or the ability to articulate, at its distal end, in a direction away from its longitudinal axis. The punch can also be termed a catheter, needle, or cannula. The punch is generally fabricated from stainless steel and comprises an outer tube, an intermediate tube, a central stylet wire, and a distal articulating region. The deflecting or articulating mechanism is integral to the punch. The punch, needle, or catheter is sufficiently rigid, in an embodiment, that it can be used as an internal guidewire or internal guide catheter. The punch is useful for animals, including mammals and human patients and is routed through body lumens or other body structures to reach its target destination.

In an embodiment, the punch comprises a core wire or stylet, an inner tube and an outer tube. The inner tube can comprise a sharpened distal end to facilitate tissue puncture. The sharpened end can comprise bevels, facets, conical sections, sharpened blade-like structures, or the like. The core wire or stylet can be blunted at the distal end to prevent damage to structures such as tissue, the sheath, or the dilator (obturator) during advancement of the endoluminal punch, caused by the sharpened distal end of the endoluminal punch. In an embodiment, the stylet can be removable or non-removable. In some embodiments, the stylet can have a large diameter to minimize trauma and shield sharp structures on the distal tip of the endoluminal punch. The endoluminal punch further comprises a hub at its proximal end which permits grasping of the punch and can also include a stopcock or valve to serve as a lock for the stylet, as well as a valve for control of fluid passage into and out from the innermost lumen within which the stylet or inner core wire resides. The hub can further comprise additional ports to facilitate the administration or withdrawal of fluids or pressure measurement. The additional ports can be terminated with Luer lock connectors or with flexible lead lines terminated with Luer lock connectors, stopcocks, or the like. The proximal end further can comprise one or more control mechanisms to manipulate the amount of articulation at the distal end of the catheter. The proximal end further is terminated with a female Luer or Luer lock port, which is suitable for attachment of pressure monitoring lines, dye injection lines, vacuum lines, a combination thereof, or the like. Other structures can be provided to alter the distal tip of the endoluminal punch such as changing it from blunter and less traumatic to sharper and more capable of tissue penetration. Such distal tip altering structures can include a piercing stylet which has an extremely sharp distal end or which transmits energy to the distal tip of the endoluminal punch. The energy can be in the form of simple manually applied force, mechanical vibration, mechanical rotation, ultrasound, high intensity focused ultrasound, electrical power to heat the distal tip, cryogenic energy, laser energy, and the like. The distal tip altering structure can comprise a quick release or controlled retraction mechanism which can be without feedback or control or it can be responsive to measurements of force, tissue properties, or the like.

Other embodiments of the inventions comprise methods of use. Keeping the method of use as close to current techniques is preferable since it reduces the learning curve and physician confidence in the procedure. The general procedure comprises placing a guidewire beyond the right atrium via a percutaneous access point in the right femoral vein or jugular vein. A transseptal introducer is advanced over the guidewire, the transseptal introducer comprising a sheath and a dilator (or obturator). The dilator or obturator further comprises a shaft, a tapered distal tip, a central through-lumen, and a hub affixed to the proximal end of the shaft. The sheath comprises a hemostasis valve to seal the dilator shaft, a sideport with stopcock communicating with the central lumen of the sheath, and the like. The sheath and the dilator can comprise a pre-formed curve near the distal end. The guidewire is next removed and a transseptal punch or other endoluminal punch is advanced through the central lumen of the dilator or obturator. The transseptal punch with the transseptal introducer riding on its back can be targeted at a specific site on the interatrial wall, generally in the area of the Fossa Ovalis. The tissue is tented by the dilator to stretch the tissue at the target site and exert a crossing force on the tissue. The transseptal punch is preferably retracted within the blunt distal tip of the obturator to prevent any chance of unwanted or inadvertent tissue perforation. Once the target is secured, the transseptal punch is advanced distal to the distal tip of the obturator thus exposing it to the tissue and causing cutting of the tented tissue. The transseptal punch and obturator/sheath are advanced across the tissue to gain access to the other side. The transseptal punch and dilator can be removed at this time to provide a pathway through the sheath or a guidewire can be reinserted to provide a track for subsequent catheterizations.

In another embodiment, the core wire, obturator or stylet is sharpened and serves as a tissue punch. In this embodiment, the distal end of the hollow tubes of the punch are blunted and made relatively atraumatic. Once the core wire punch has completed tissue penetration, the outer tubes are advanced over the central punch wire through the penetration and into the left atrium. In another embodiment, a pressure monitoring device such as a catheter tip pressure transducer, or a pressure line terminated by a pressure transducer, can be affixed to a quick connect, generally a Luer fitting, at the proximal end of the punch hub. By monitoring pressure, it is possible to determine when the distal end of the punch has passed from, for example, the right atrium into the left atrium, because the pressure versus time curves in these two chambers are measurably, or visually, different. The proximal end of the hub further has provision for attachment to a dye injection line for use in injecting radiographic contrast media through the central lumen of the punch. Typically a manifold can be attached to the Luer fitting on the proximal end of the hub, the manifold allowing for pressure monitoring, for example on a straight through port, and for radiopaque dye injection, for example through a side port. A stopcock, or other valve, can be used to control which port is operably connected to the central lumen of the punch.

In some embodiments, the inner tube, the outer tube, or both can have slots imparted into their walls to impart controlled degrees of flexibility. The slots can be configured as "snake cuts" to form a series of ribs with one or more spines. The spines can be oriented at a given circumferential position on the outer tube, the inner tube, or both. The spines can also have non-constant orientations. In some embodiments, only the outer tube is slotted. The slots can be generated within the distal portion of the outer tube where the curve is generated. This flexible distance can range between about 0.5-cm and 20-cm of the end and preferably between about 1-cm and 12-cm of the distal end. The slot widths can range between 0.001 inches and 0.010 inches with a preferable width of about 0.001 to 0.005 inches. In exemplary embodiments, the slot widths are about 0.003 inches. In some embodiments, it is desirable to have the outer tube bend in one direction only but not in the opposite direction and not in either lateral direction. In this embodiment, cuts can be made on one side of the outer tubing within, for example, the distal 10-cm of the tube length. Approximately 10 to 30 cuts can be generated with a width of approximately 0.001 to 0.015 inches. The cut depth, across the tube diameter from one side, can range between about 1% and 90% of the tube diameter. In an embodiment, the cut depth can be approximately 0.4 to 0.6 of the tube diameter with a cut width of about 0.005 inches or less. A second cut can be generated on the opposite side of the tube wherein the second cut is approximately 0.005 inches or less. In an embodiment, the outer tube can be bent into an arc first and then have the slots generated such that when the tube is bent back toward the 0.005-inch wide cuts, the tube will have an approximately straight configuration even through each tube segment between the cuts is slightly arced or curved.

The steerable needle, in other embodiments, can comprise monitoring systems to measure, display, announce, record, or evaluate operating parameters of the steerable transseptal punch. In an embodiment, the steerable transseptal punch can comprise strain gauges to measure the force being applied by the user to bend the needle. A torque gauge can also be comprised by the system to measure torque being applied to the control knob or the torque being applied by the distal curvature movement. The strain gauge or torque gauge can be affixed within the hub or elsewhere within the steerable transseptal punch to measure compression or tension forces. This information can be displayed in the form of a readout device, such as a digital display of the force or torque. The number of turns can be counted and displayed by, for example, a Hall-Effect sensor, mechanical counter, or the like. In an embodiment, the force or toque can be correlated to the angle of deflection at the distal end, the number of turns applied to the control knob, or both. The readout can be digital or analog and can be affixed to the hub or can be wirelessly received and displayed on external equipment such as a smart phone, computer, tablet computer, panel display, or the like. The wireless technology can, for example, comprise Wi-Fi, Bluetooth®, or other standardized protocols. The human interface can, in other embodiments, comprise audible feedback such as a simple beep or tone, or it can be more sophisticated and provide information using language callouts such as force, turns, torque, or the like.

In operation, the procedure is to advance a steerable transseptal punch, with a tissue piercing stylet affixed in place, through a transseptal introducer that has already been placed. The steerable transseptal punch is articulated to generate the proper curve, as determined under fluoroscopic or ultrasound guidance. The steerable transseptal punch transseptal introducer assembly is withdrawn caudally out of the superior vena cava and into the right atrium of the heart. Proper location, orientation, tenting, and other features are confirmed. Radiopaque dye can be injected through the steerable transseptal punch to facilitate marking of the fossa ovalis or blood flow around the distal end of the steerable transseptal punch. Pressure measurements can also be taken through the lumen of the steerable transseptal punch to confirm tracings consistent with the right or left atrium of the heart. Once proper positioning has been confirmed, a safety is removed from the stylet hub and a button on the stylet hub is depressed or actuated to cause the sharpened stylet tip to advance out beyond the distal end of the steerable transseptal punch. This sharpened stylet punches through the fossa ovalis and the septal tissue pulls over the stylet, over the inner tube, and over the obturator or dilator of the transseptal introducer. At this point, the sharp stylet is released and retracts proximally within the steerable transseptal punch. The transseptal introducer is now within the left atrium of the heart and the steerable transseptal introducer can be withdrawn from the lumen of the obturator.

FIG. 3A illustrates another embodiment of a dilator and introducer for endoluminal punch, which can be used with both steerable and non-steerable punches. The introducer 300 comprises an introducer shaft 302, having a tapered or faired tip 324 and a dilator 304, further comprising a central lumen 306, an internal stepdown or shoulder 308, to serve as a stop for an endoluminal punch, a small diameter tip lumen 320, a radially outwardly directed, side slot 310, a cutting element 316 disposed within the central lumen 320. The cutting element comprises a spring arm 318, a sharp edge (a blade portion) 314 on the radially outwardly facing edge of the cutting element, and an anchor ring 312 for fixing the cutting element within the lumen of the tapered dilator tip 324.

The side slot 310 communicates from the tip central lumen 320, through the wall of the tip, to the exterior of the tapered dilator tip 324 and permits the cutting element 316 and its spring arm 318 to move radially outward beyond the central lumen 320, wherein it resides when at rest, biased by the spring arm 318. The cutting element 316 can be fabricated from stainless steel, nitinol, titanium, cobalt nickel alloy or the like.

FIG. 3B illustrates the introducer and dilator of FIG. 3A with an endoluminal punch 334 having been inserted through the central lumen 306 and 320 as far as possible with a stepdown 322 on the endoluminal punch engaging the stepdown 308 in the lumen 306. A needle portion, including a small diameter portion 322 of the endoluminal punch 334 and its sharp tip 330 projects through the lumen 320 and forces the spring arm 318 and the cutting element 316 to move radially outward through the slot 310. The sharp edges 314 are configured to cut tissue as the dilator is advanced through tissue thus allowing a larger diameter incision to be made than could be made with the endoluminal punch, by itself.

Thus the endoluminal punch system has the cutting element (316) biased to the position within the dilator lumen of the tapered dilator tip and the punch inner tube is operable to force the cutting element to the position external to the tapered dilator tip upon passage of the distal end of the punch inner tube through the tapered dilator tip. The endoluminal punch comprises a punch outer tube having a first diameter and a punch inner tube having a second diameter smaller than the first diameter, and inner tube extends distally from a proximal end of the outer tube. The dilator lumen of the tapered dilator tip is configured to accept passage of the punch inner tube, but is too small to allow passage of the punch outer tube, such that the dilator lumen of the tapered dilator tip has a third diameter smaller than the first diameter of the punch outer tube and larger than the second diameter of the punch inner tube. the punch inner tube is operable to force the cutting element radially to the position external to the tapered dilator tip upon passage of the distal end of the punch inner tube through the tapered dilator tip.

In this embodiment, the endoluminal punch 334 can be inserted through the introducer 300 further comprising the dilator 304 or obturator which can further comprise the cutting element 316 tipped with 314, which can project laterally to assist with cutting tissue surrounding the tapered tip of the dilator. The cutting element can comprise a sharp blade like structure. The cutting element can be spring loaded so that, when something is advanced through the internal lumen 306 of the dilator 304, the blade 316 is forced radially or laterally out of the way and projects laterally outward. This way, the lateral cutting blade 316 with the sharp edge 314 is restricted or shielded inside the dilator 304 partially or completely when nothing is inserted through the lumen 320. A segment of the lateral cutting blade can be dispositioned within the lumen 320 to facilitate outward advance of the cutting blade or apparatus when another object is forced through the lumen. This feature can be useful in penetrating tissue with the endoluminal punch and then following it with the larger diameter dilator 304 and introducer or catheter sheath 302. The laterally projecting blade or cutter 316 can enlarge a hole in tissue already incised by the endoluminal punch, thus facilitating passage of the dilator 304 and introducer sheath 302 through the hole in the tissue. Conditions can occur in patients who have had prior procedures and therefore incur scar tissue on the interatrial septum, for example, and this tissue is very difficult to cross. Further, it appears possible that patients who have been in long-term persistent atrial fibrillation incur morphological changes to the myocardium in the interatrial septum, and perhaps other parts of the atrial tissue, that cause it to become tough and difficult to penetrate.

The endoluminal punch system of FIGS. 3A and 3B can be used by first inserting the dilator, in its straight configuration, into the sheath (which may be straight or pre-curved), and then navigating the assembled sheath and dilator to the target location. (The sheath can be inserted empty, and the dilator can be inserted into the sheath after the sheath distal end is proximate the target location). Then the endoluminal punch, in a straight configuration, is inserted into the dilator lumen and translated through the dilator until the distal end of the punch is proximate the distal end of the dilator. The assembled system is then pushed against the target tissue to be punctured (which may entail operating steering features of one of the components, preferably the punch), and the punch is advanced distally through the dilator lumen, including the lumen of the tapered dilator tip, such that the inner tube of the punch passes through the lumen of the tapered dilator tip until the point of the punch inner tube penetrates the target tissue. Passage of the punch inner tube through the lumen of the tapered dilator tip results in impingement of the punch inner tube on the cutting element, and forces it radially outward until the sharp edge is external to the tapered distal tip and exposed to tissue. The punch creates an initial puncture in the target tissue, and the dilator is then advanced distally into the target tissue until the tapered distal tip and exposed cutting element enter the target tissue to enlarge the initial puncture and allow the dilator to pass through the puncture. The sheath can then easily be passed through the puncture. The punch and dilator can then be removed to allow therapeutic or diagnostic instruments through the sheath into the target tissue. The cutting element may be retracted before withdrawing by first withdrawing the punch.

A system which uses the cutting dilator can further comprise a guidewire, a catheter, a device delivery system, a delivery system for an implantable medical device, a catheter providing a support function for an implant, therapy, diagnostic procedure, or the like.

In other embodiments, the endoluminal punch can comprise a blunted distal end with a slot at the end to allow a blade to project out the distal end of the steerable endoluminal punch. The blunted distal end can be retracted to expose the blade for cutting or the blade can be advanced out the distal end through the slot which would appear like the window of an observatory. The blade can be fixed or it can oscillate or rotate as described herein.

FIG. 1 illustrates a transseptal introducer system 100 with endoluminal punch, comprising a hub 102, an O-ring 114, a jackscrew 112, a control knob 110, a spring 136, a stylet 108, an inner tube 104, an outer tube 106, an inner tube anchor 130, a hub stopcock coupler 132, a stopcock 134, a flow lumen 128, a vibratory driver 116, a power source 120, an electrical bus 126, a controller 124, a control switch, and a central vibrator shaft 122.

The vibratory driver 116 can operate in the subsonic range (less than about 0.1 Hz) all the way up through the ultrasonic range (5-50 kHz), and preferably in the range of about 0.1 Hz to 100 Hz, and more preferably in the range of about 0.5 Hz to 10 Hz. Power levels in the range of about ½ Watt to about 20 Watts can be used with a preferred range of about 2 Watts to about 6 Watts. In the illustrated embodiment, the endoluminal punch is of the steerable variety wherein the control knob 110 can generate off-center forces at the tip to bend a region of outer tube 106 which is selectively made more flexible than the rest of the shaft. In the illustrated embodiment, the vibratory driver 116 is affixed to the hub 102 which is affixed to the anchor 130. The shaft 122 of the vibratory drive 116, which can comprise a hollow lumen (not shown) to allow for fluid transport therethrough, is affixed to the inner tube 104 such that the inner tube 104 is vibrated back and forth axially a small amount which is transmitted to the tip causing a generally axial but also sideways vibratory motion that can be used to promote tissue incision.

FIG. 1 illustrates embodiments wherein a vibratory device 116 can be affixed to the hub of the endoluminal punch system 100, which may be a steerable punch or a non-steerable punch. The vibratory device shaft 122 can oscillate back and forth along the longitudinal axis, in an embodiment. Axial vibratory movement of the hub can be transmitted down the length of steerable endoluminal punch shaft such that the distal tip of the steerable endoluminal punch vibrates back and forth along its longitudinal axis. A translator mechanism can be provided which turns this axial vibration into vibration in a direction lateral to that of the longitudinal axis of the steerable endoluminal punch. The vibratory device can comprise a power source derived from a control console, batteries, a wall outlet, or the like. The vibratory device can be operably connected to the power source using a cable, wiring harness, or the like. In these embodiments, the vibratory device 116 and its power and control subcomponents can be integrated into the hub of a needle system 100.

In these embodiments, the vibratory device 116 is directly or indirectly affixed to the anchor 130 of the inner tube 104, the anchor 130 in turn being affixed to the hub 102. The inner tube 104 is affixed to the shaft 122 of the vibratory device and moves therewith. Thus, the inner tube 104 is separated from the hub 102 by the vibratory structure 116. The vibratory mechanism 116 can comprise a loudspeaker type linear movement device, an off-center weight which is rotated about an axis by a motor, a piezoelectric driver, a pneumatic driver, or the like. These systems, in some embodiments, require an input comprising a sine wave structure, or other, which can be controlled in terms of amplitude and frequency and wave shape. In these embodiments, the anchor can be made to vibrate on axis, thus transmitting the vibrator energy to the distal tip of the device through the inner tube and control rod or rods at the distal portion of the steerable endoluminal punch. Since the inner tube is affixed to the outer tube in an off-center manner near the distal end of the steerable endoluminal punch, the distal end of the steerable endoluminal punch will operably vibrate in a lateral direction to the axis of the steerable endoluminal punch. This vibration (oscillatory) energy can provide assistance in cutting through tissue beyond that possible with a static device. The vibratory transducer can be operably connected to a power supply and controller by means of a cable to a power source external to the hub of the steerable endoluminal punch and the power supply can comprise batteries and signal conditioning apparatus and/or software within the steerable endoluminal punch hub. The frequency of vibration can range from less than 1 Hz to ultrasound frequencies of about 40-kHz or more.

In other embodiments, the vibratory apparatus can be affixed to, and operably connected to, a separate control rod or wire disposed within a lumen of the steerable endoluminal punch and routed from a driver at the proximal end to a point at or near the distal end of the steerable endoluminal punch. In these embodiments, it is beneficial to affix the driver of the vibratory apparatus to the proximal end of the steerable endoluminal punch. This control rod or wire can transmit the energy to the distal end of the steerable endoluminal punch wherein it can be used to drive lateral movement, axial movement, rotary movement, or a combination thereof to facilitate tissue penetration and crossing through a hole larger than that which can be made with the steerable endoluminal punch alone, without the energy assistance. The wire or control rod can be affixed to the distal end of the steerable endoluminal punch in an off-center way to generate lateral tip movement in an oscillatory fashion. In an embodiment, the axial to lateral translation system can comprise mechanisms such as, but not limited to, an inner protrusion (cam) near the distal tip that causes a lateral jog when impacted by an oscillating axial linkage driven from the proximal end of the steerable endoluminal punch. In other embodiments, the distal tip can comprise a rotary crankshaft to generate lateral motion.

In an embodiment, the vibratory apparatus is affixed to the proximal end of the steerable endoluminal punch. The shaft of the vibratory apparatus is affixed to a transmission wire or rod which is constrained within a lumen of the steerable endoluminal punch to move reciprocally along the longitudinal axis of the steerable endoluminal punch and is further constrained not to move substantially radially relative to the steerable endoluminal punch. The wire or rod can project out the distal end of the steerable endoluminal punch an amount equal to approximately 0.010 inches and 0.500 inches with a preferred protrusion of about 0.015 inches to about 0.050 inches. The distal tip of the wire or control rod can comprise configurations such as, but not limited to, rounded, squared off beveled, tapered point, trocar-shape, or the like. The distal tip of the steerable endoluminal punch can likewise comprise structures such as, but not limited to, pyramids, tapered points, beveled points, fully flat, blunted, blunted with rounded edges, and the like. The axial wire or control rod can be configured to retract upon control by the user and then extend distal to the distal tip of the steerable endoluminal punch when activation is required.

Figure 2:
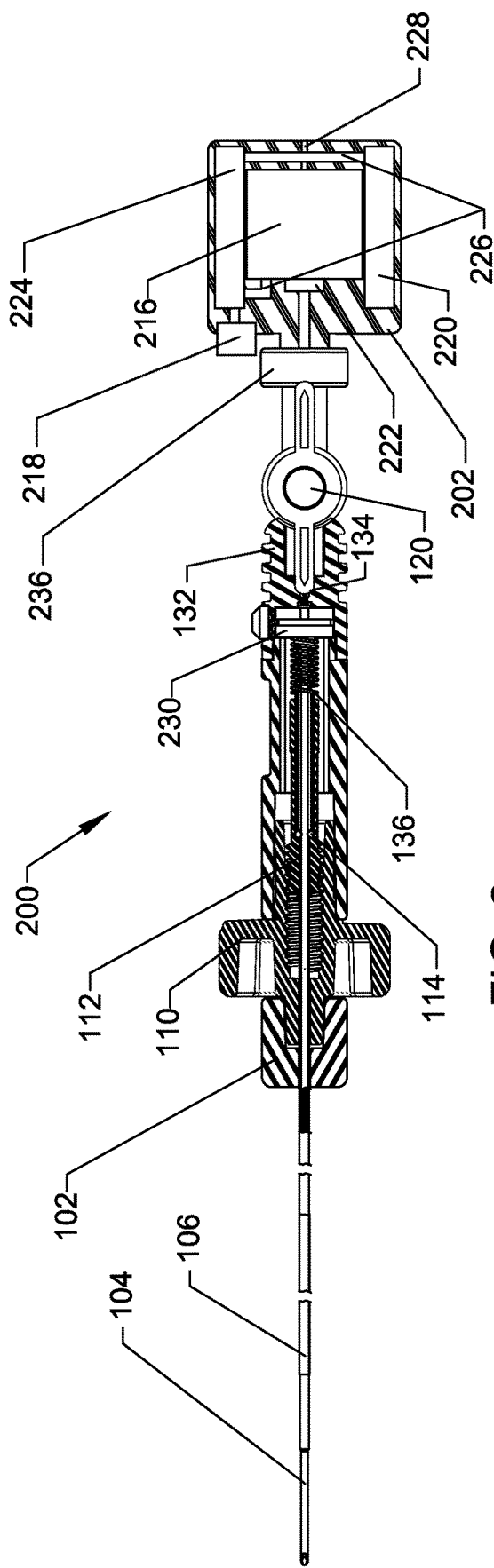
FIG. 2 illustrates a steerable endoluminal punch, as viewed from the side in cross section, whereby a vibratory actuator is operably connected to the proximal end of the hub of the steerable endoluminal punch.

FIG. 2 illustrates another embodiment of the steerable endoluminal punch 200 system wherein the vibratory structure 216 is affixed to the proximal end of the steerable endoluminal punch 200. The steerable endoluminal punch system 200 comprises the inner tube 104, the outer tube 106, the hub 102, the control knob 110, the jackscrew 112, the O-ring 114, the spring 136, the adapter 132, the stopcock 120, and the central lumen 134, which operably communicates between the lumen of the inner tube 104 and the central lumen of the stopcock 120. The steerable endoluminal punch system 200 further comprises an ultrasound driver coupler 236, an ultrasound driver 216 having a central moving shaft 222, a power supply 220, an electrical bus 226, a control switch 218, a control system 224, a case 202, and a central lumen 228.

The coupler 236 connects the shaft 222 to the stopcock 120 and therefore the hub 102 of the steerable endoluminal punch. In this configuration, the energy is transmitted through the entire steerable endoluminal punch in an axial fashion but does not cause any relative movement between the inner 104 and outer 106 tubes.

The energized steerable endoluminal punch system 100 and 200 configurations can be used for tissue punch, incision, or penetration, apparatus, etc. They can, in other embodiments, comprise the structure of a guidewire, a stiff track over which other devices or catheters are advanced, an introducer, a catheter, a delivery catheter for an implant or fluids, a therapeutic catheter, a diagnostic catheter, a catheter to support other procedures, or the like. The steerable endoluminal punch can be monitored using fluoroscopy and radiopaque markers affixed or integral to the steerable endoluminal punch. It can also be monitored using ultrasound guidance such as with transesophageal echocardiography, intracardiac echocardiography, real-time three-dimensional echocardiography from transducers and systems affixed to the steerable endoluminal punch.

In other embodiments, vibration can be generated by an ultrasonic transducer mounted within the steerable endoluminal punch tubing. An ultrasonic wire can be disposed along the steerable endoluminal punch tubing through a lumen. An ultrasonic transducer can be affixed to the distal end of the steerable endoluminal punch.

Figure 4:
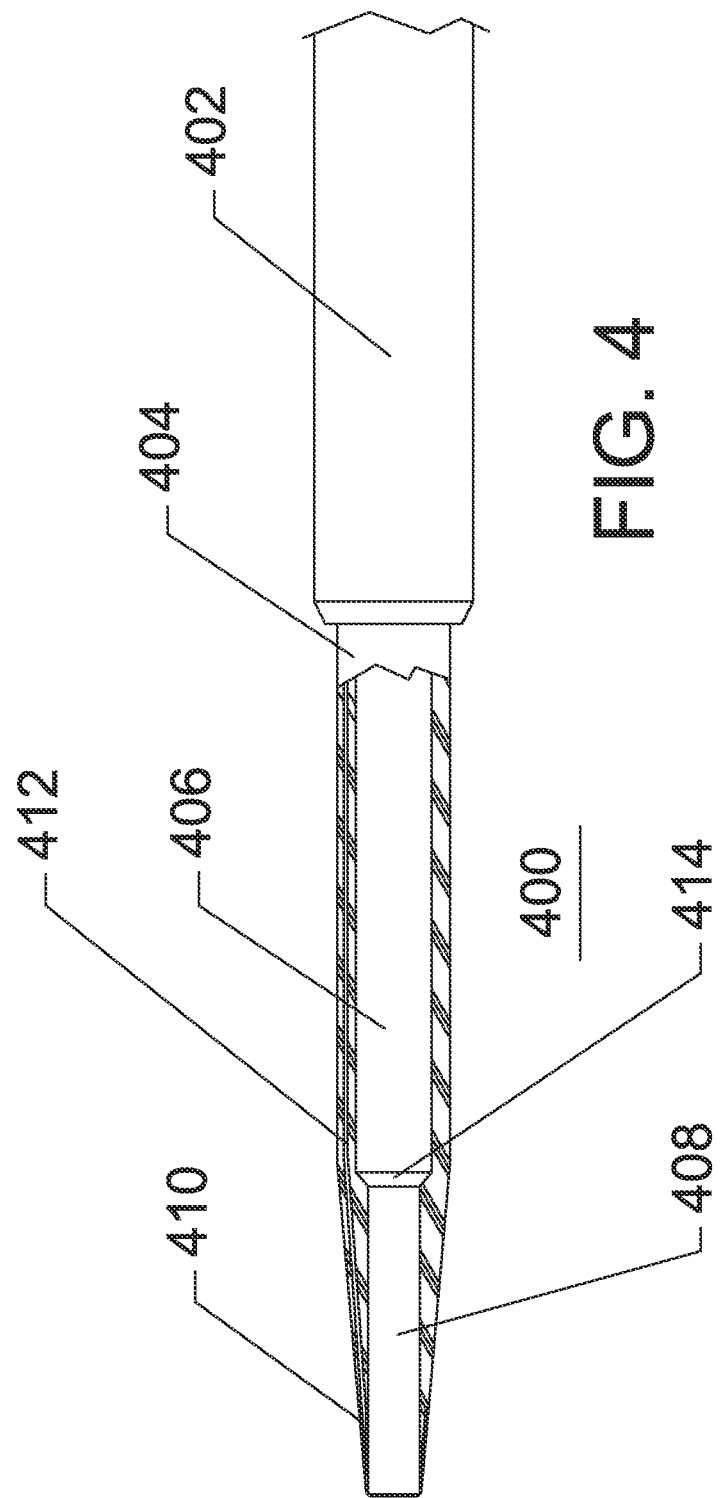

FIG. 4 illustrates a side view, in partial breakaway, of an introducer system 400 comprising a sheath 402, further comprising a central lumen (not shown), and a dilator 404 further comprising a proximal central lumen 406, a step-down 414, a distal tip lumen 408, and a side lumen 412. In some embodiments, a control linkage (not shown) can be routed through the side lumen 412 such that it is constrained to move axially. Energy drivers, such as 116 and 216 described herein can move the control linkage (not shown) to move elements at the distal end of the dilator 404. In other embodiments, the side lumen 412 can comprise an electrical bus (not shown) which operably connects to an electrode 410 proximate the distal tip of the dilator to generate energy and promote tissue penetration. Such energy generation can comprise modalities such as, but not limited to, microwave radiation, radiofrequency radiation, high frequency focused ultrasound (HIFU), and the like. Energy ranges for the radiofrequency ablation can range from about 2 to about 20 Watts with a preferred range of about 5 to 15 Watts. Energy ranges in the ultrasonic system can range from about 1 Watt to about 20 Watts with a preferred range of about 2 Watts to about 10 Watts.

In some embodiments, such as those configured for delivery of radiofrequency energy to the tissue, an electrode, typically made from conductive, biocompatible, metal, can be affixed to the distal tip of the dilator. The electrode can be configured as a ring, a line or an electrode-patch on the tapered part of the exterior of the dilator tip proximate its distal end. The electrode can be electrically, operably coupled to an electrical bus running through the dilator wall which can then be operably coupled to an RF generator by way of a cable attached to the hub of the endoluminal punch.

The method of use of the RF introducer dilator tip is that the tip electrode comprises an element disposed along one side of the dilator tip or in the form of a ring electrode. A plurality of electrodes can be disposed along or around the dilator tip to provide for increasing the size of the hole which the dilator can create in tissue. The center lumen of the dilator can comprise a removable or axially advanceable steerable endoluminal punch. The dilator tip and surrounding sheath can be advanced against tissue and held there with modest force such that the tissue is tented, dented, poked, or dimpled by the tip of the dilator. The steerable endoluminal punch tip can next be advanced distally to the dilator tip to perforate the tissue against which the dilator tip is resting. Should this cut in the tissue resulting from steerable endoluminal punch advancement not be sufficient to allow the dilator tip to pass through the incision in the tissue created by the steerable endoluminal punch under modest force applied by the operator or robot, the tip electrode can be energized using Ohmic heating, RF energy, or the like. This energy application can burn a hole of sufficient size to permit advancement of the dilator tip through the tissue. The steerable endoluminal punch can be retracted proximally back inside the distal tip of the dilator at this point for increased safety so as not to puncture tissue on the other side of the cavity into which the steerable endoluminal punch and dilator/sheath are being advanced. The RF energy can be set to discontinue once the electrode no longer touches tissue, or after one of the more proximal electrodes of an array then touches tissue. A timer can also be used to cut power to the tip electrode after a pre-determined period of time has passed.

FIG. 5A illustrates the result of using a pointed object to poke a hole in tissue (upper image) and with further configuration to dilate that hole to the size of a transseptal punch, which is 0.032 inches in diameter, as shown in the lower image. The tissue is tightened as it stretches and it does not readily split or incise due to the lack of stress risers resulting from a poke hole being dilated.

FIG. 5B, upper image, illustrates the result of using a half-round blade or half-trephine to cut a semicircular slice in tissue. The trephine can have a flat distal edge or a beveled or other complex shape distal edge. This semicircular slice can fold outward to its full diameter with little or no stress imposed due to dilation, as shown in the bottom image. Additional dilation of this hole can be performed with less force than needed to dilate the hole created in FIG. 5A. The cutting edge of the endoluminal punch can beneficially be described as being formed from a circular tube that is beveled at its distal end. The walls of the endoluminal punch can be sharpened by forming facets or a conical fairing down to a sharp distal edge. If facets are employed, it is possible to generate an extremely sharp tip on the distal edge of the endoluminal punch. One facet on each side can perform cutting of the semicircular tissue incision but it is also beneficially possible to use two or more facets on each side of the cutting edge to maximize sharpness. The facets can be created by grinding, by electron discharge machining (EDM), by laser cutting, by regular machining, or the like. The inner tube that is terminated at its distal end with the sharp structure can be fabricated from 304 stainless steel, 316 stainless steel, or a precipitation hardening stainless steel like 17-7 PH to allow for heat treating and increased strength in these sharp regions.

Note that a stubby blunt stylet, expandable or non-expandable, can be used to shield the sharp pointed distal end of the endoluminal punch from skiving plastic off the wall of the introducer dilator or from getting dulled by the same interaction. It is generally beneficial to align the direction of curvatures of the endoluminal punch with that of the introducer and dilator.

FIG. 5C upper image, illustrates the result of using the half round blade from FIG. 5B but further enhanced with a cutting dilator (FIG. 3A and FIG. 3B) that can generate a slot, shown radially disposed in this FIG. 5B. The radially oriented slot can protrude in various angles to generate maximum tissue splitting with minimal tissue dilation. Thus, larger catheters can pass through the tissue fenestration created by the endoluminal punch used to generate this hole.

FIG. 6A illustrates a side view of an endoluminal punch distal end 600 comprising an inner tubing shaft 602 further comprising a lumen 606 and a tubing wall 604. The distal end further comprises a sharp tip 612, a bevel 610, and one or more facets 608, the bevel 610 and facets 608 being features cut into the tubing wall 604.

FIG. 6B illustrates a front view of the endoluminal punch 600 showing the tubing 602, further comprising the wall 604, the lumen 606, the sharp tip 612, the facets 608, and a bevel 610.

FIG. 7A illustrates a side view of an endoluminal punch 700, comprising the punch tubing or shaft 702, a hub 704 further comprising a control knob 710, a directional pointer 714, and a hub connector 706. The hub connector 706 comprises a proximal housing 708, a distal housing 712, a spring element 724 (not shown), and a distal end connector 732. The hub connector 706 can be bonded, mechanically affixed, welded, or formed integral to the hub 704. The hub connector 706 can also comprise a lock 726 (not shown) or safety clip 722 (not shown), which can be removed, applied, engaged, or disengaged. The hub connector 706 is shown spring biased into its maximum length to pull the endoluminal punch hub 704 as far as possible proximal to the proximal connector 758 of the dilator hub 762 (see FIG. 7B). The endoluminal punch 700 further comprises a punch shaft or outer tubing 702, an inner tube 732, which can project distally beyond the outer tubing 702, and a flexible region 720.

In all embodiments disclosed herein, a flexible region is defined as a region that possesses flexibility greater than that of proximally or distally disposed adjacent regions. The flexible region is a region at the distal end of the outer tube that is significantly more flexible and susceptible to deflection than the remaining proximal region of the outer tube.

In the embodiment where a lock 726 is included, the lock 726 can be configured to be released by the user and then re-engage when the spring element 724 expands a predetermined amount, thus preventing a second advancement of the endoluminal punch 700 until the lock 726 is selectively released again by the user.

FIG. 7B illustrates a side exterior view of an introducer 750 further comprising a sheath 752 and a dilator 760 further comprising a dilator tapered distal end 764. The Luer lock distal end 734 of the endoluminal punch 700 permits attachment and removal of the endoluminal punch 700 from a hub 762 of the dilator 760, which comprises removable part of a catheter or introducer 750.

In some embodiments, the compressed spring element 724 can activate a trip, or limit, switch (not shown) which causes the endoluminal punch 700 to retract inside the dilator lumen without any control on the part of the user. In other embodiments, the compressed spring element 724 can be coupled to a timer that releases a catch (not shown) and causes retraction of the endoluminal punch 700 inside the dilator lumen.

The bias force generated by the spring 724 can range from about 0.25 pounds to about 5 pounds just prior to full compression. In preferred embodiments, the spring 724 bias force can range from about 0.2 pounds to about 1 pound just prior to full compression, which can be approximately 0.2 inches to 0.5 inches of travel, in the illustrated embodiment.

The spring 712 can, in other embodiments, further be replaced with a magnetic force generation system, pneumatic force generator, hydraulic force generator, motorized (e.g. electric powered) force generator, or the like.

Figure 8A:
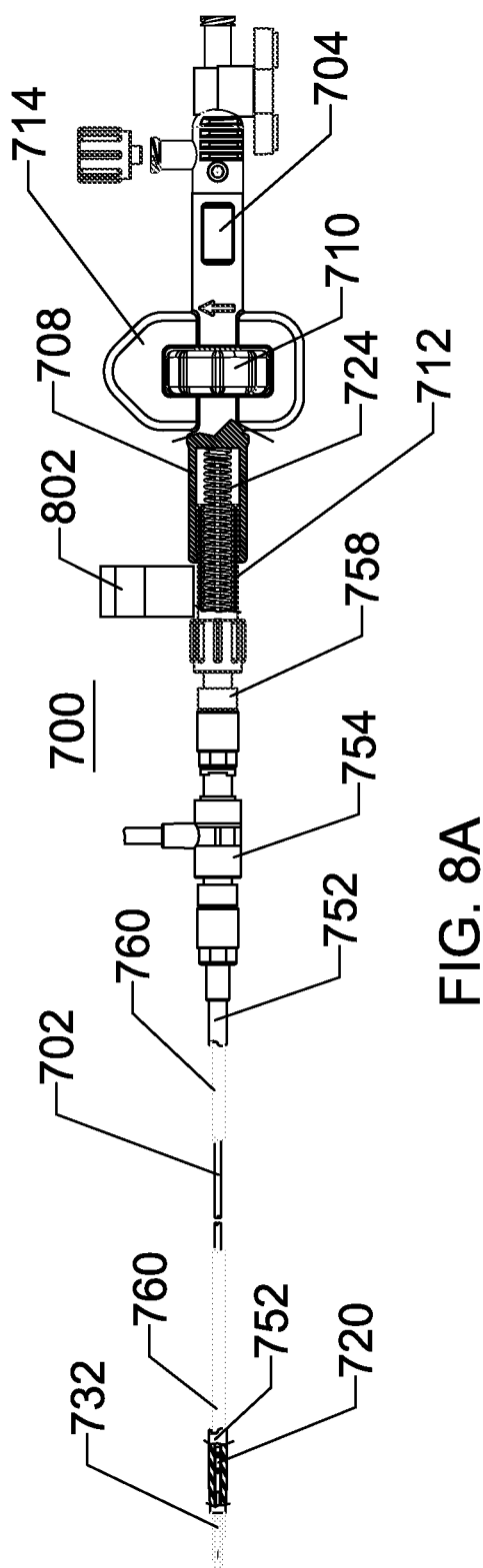
FIG. 8A illustrates a side view, in partial breakaway, of the endoluminal punch of FIG. 7A inserted through the introducer of FIG. 7B.

FIG. 8A illustrates a side view, in partial breakaway, of the endoluminal punch 700 inserted through the central lumen of the dilator 750. The distal end 732 of the endoluminal punch 700 of FIG. 7A is shown retracted inside the dilator tip 762. The distal end of the endoluminal punch 700 is operably connected to the hub 704 by the tubing 702. The spring element 724 is shown in this breakaway with maximal expansion and minimal compression. The distal connector 734 of the punch is affixed to the connector base 712. The connector base 712 is constrained concentrically and slides axially within the hub sleeve 708.

Figure 8B:
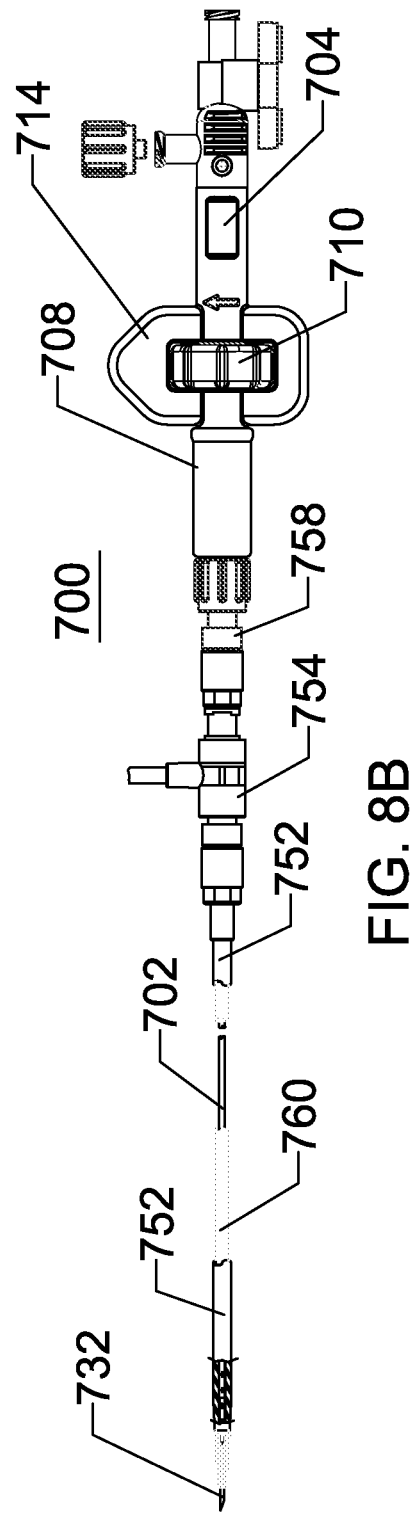
FIG. 8B illustrates a side view of the distal end of the endoluminal punch of FIG. 7B with the safety clip removed and the tip advanced distally into the dilator to expose the sharp end of the endoluminal punch distal to the dilator tip.

In the embodiment shown in FIGS. 8A and 8B, the user removes the clip when ready to activate the tissue incision or puncture mechanism. The user grasps the hub 704 and pushes against the tissue with the introducer 750 and its dilator 760 riding along. The tissue pushes back against the dilator tip 762 with greater force than the tip 732 of the endoluminal punch so the endoluminal punch distal tip 732 protrudes out the distal end of the dilator lumen and punches through the tissue. The distal end of the dilator obturator continues to build force until such time as it passes through the tissue, at which point, the endoluminal punch tip retracts inside the lumen of the dilator, or has already done so upon spring bias, depending on the strength of that spring bias. In this illustration, the safety clip 722 has been removed and/or any type of lock has been disengaged. The hub connector 706 has been compressed axially to compress the spring element 724 minimizing the distance between the endoluminal punch hub 704 and the connector 758 of the hub 762 of the dilator 760. As a result of such axial compression, the punch shaft 702 is advanced distally relative to the dilator hub 754 and the distal end of the punch shaft 732 is therefore advanced distally relative to the dilator tubing tip 764, thus becoming exposed to the patient environment and able to penetrate tissue.

FIG. 8B illustrates a side view of the distal end 800 of the endoluminal punch of FIG. 7B with the tip 732 advanced distally beyond and outside the dilator tubing tip 764. The endoluminal punch distal tip 732 is operably connected to the hub 704 by the punch tubing 702. The punch sharp distal tip 732 is advanced distally relative to the introducer dilator and is exposed beyond the distal end 764 of the dilator 760 by forcing the needle hub 704 distally relative to the dilator hub connector 758. In this configuration, the sharp tip 732 of the endoluminal punch 700 is capable of penetrating or incising tissue. The spring element 724 compresses and builds energy to bias the distal tip 732 proximally so that when the endoluminal punch hub 704 is released, unlatched, or otherwise freed, the spring element 724 quickly retracts the punch sharp distal tip 732 inside the distal end 764 of the dilator 760 to render the tip 732 atraumatic and unable to penetrate tissue.

FIG. 9 illustrates a side view of the distal end of the endoluminal punch 600 comprising a removable protective blunt stylet 900. The blunt stylet 900 comprises the stylet shaft 902 and a stylet hub 904 (not shown) which is affixed to the proximal end of the stylet shaft 902. The stylet shaft 902 comprises an atraumatic tip 906. The stylet hub 904 can be removably affixed to the proximal end hub (not shown) of the endoluminal punch 600 using methods such as, but not limited to, a bayonet mount, Luer lock, threaded attachment, a clip, or the like. The endoluminal punch 600, as illustrated, is steerable and includes laterally oriented slots in a flexible region to facilitate flexibility. The endoluminal punch 600 comprises an outer tube 620, an inner tube 602, a plurality of facets 608, a lumen 606 (not shown), and a distal point 612.

Referring to FIG. 9, the blunt stylet shaft 902, at its distal end, is preferably of a diameter sized to slidably fit through the lumen 606 of the endoluminal punch 600 but yet retain sufficient size so as to be large enough to shield the tip 612 as well as edges 610 and sharp facets 608 of the endoluminal punch 600 from tissue or catheter tubing through which it might be inserted. In other embodiments, the distal end 906 of the blunt stylet shaft 900 can be expandable slightly so that it can pass through the inner tube lumen 606 but then expand diametrically to more completely shield the sharp tip 612 and any features or facets 608 of the endoluminal punch. This can be accomplished, in an embodiment, by making the stylet shaft 902 from hollow tubing which can be slit in a variety of patterns and then spring biased to a larger diameter configuration with expanded slits. The expansion need only be in the range of 0.002 to 0.020 inches with a preferred range of 0.003 to 0.010 inches. The stylet shaft 902 can be fabricated from stainless steel, nitinol, PEEK, PET, ABS, polyurethane, polycarbonate, or the like. In a preferred embodiment, the lumen 606 through which the stylet passes is about 0.023 inches in diameter. The expansion can result from inflation of a balloon like structure, spring bias on leaf-like or cage-like structures, elastomeric expansion, or the like. In expandable embodiments, the external structure of the stylet distal end can beneficially be fabricated from lubricious materials so that it can be inserted through the lumen of the endoluminal punch with minimal drag or friction.

The stylet 902 in a non-expandable configuration comprises a diameter of about 0.021 to 0.022 inches resulting in a very small annular space between the stylet 902 and the inside diameter 606 of the inner tubing 604, which can, for example be around 0.023 inches. It is also beneficial that the wall of the inner tubing be as reasonably thin as possible at its distal edge to reduce any protrusions or edges that could scrape plastic or cut tissue. The wall of the inner tubing 604 can be tapered or faceted down to a minimal distance to minimize protrusions and the wall near the distal tip 612 of the inner tubing can preferentially have a thickness of about 0.001 to 0.005 inches, again to minimize catching on stretched tissue that could cause hang-up of the steerable endoluminal punch while being advanced through the tissue. The stylet shaft 902 can protrude to about 0.010 inches beyond the distal tip of the inner tube in a preferred embodiment, with a preferred range of protrusion of about 0.050 to 0.030 inches. The atraumatic distal tip 906 can be substantially hemispherical, as illustrated, or it can comprise a conic section with a round distal end or it can be squared with rounded edges or the like.

In other embodiments, a polymeric stylet 900 can further comprise a molded or otherwise formed distal tip that is formed larger in diameter than the inside diameter 606 of the inner tube 604 but is spring biased to expand outward slightly once advanced distal to the distal tip 612 of the punch. The stylet shaft 902 can comprise a hollow tube or a solid rod in cross-section.

The distal end 604 of the inner tube 602 is beneficially ground to a smaller diameter than the basic shaft 602 of the inner tube to match standard inside diameters of introducer dilators. In some embodiments, the diameter of the distal end 604 of the inner tube can be configured to have a diameter of about 0.032 inches with a preferred range of about 0.0315 to 0.0325 inches, thus matching currently marketed transseptal punches and transseptal introducer dilator lumens. In other embodiments, it is preferable that the distal end diameter 604 of the inner tube range of about 0.033 inches to 0.036 inches. This larger diameter inner tube distal end 604 has the benefit of being able to cut a larger incision in the tissue than the smaller diameter inner tube distal end 604. Furthermore, the larger diameter inner tube distal end 604 will have more strength and resistance to deformation than the inner tube distal end with a smaller outside diameter. In yet other embodiments, where the inner tube is ground to create a circumferential groove for placement of an RO marker (not shown). The 0.033 to 0.036 inch OD inner tube distal end 604 has greater wall thickness to accommodate an RO marker without compromising wall strength than does the inner tube distal end 604 with an OD of about 0.032 inches. Furthermore, the RO marker can comprise a thicker wall and thus increase its visibility if the larger diameter inner tube distal end 604 is used in fabrication of the endoluminal punch 600. This larger outside diameter of the distal end of the inner tube requires that the lumen of the dilator, at its distal end, be larger in diameter than the standard. Guidewire compatibility would be 0.035 inches rather than the current 0.032 inch capacity.

Figure 10A:
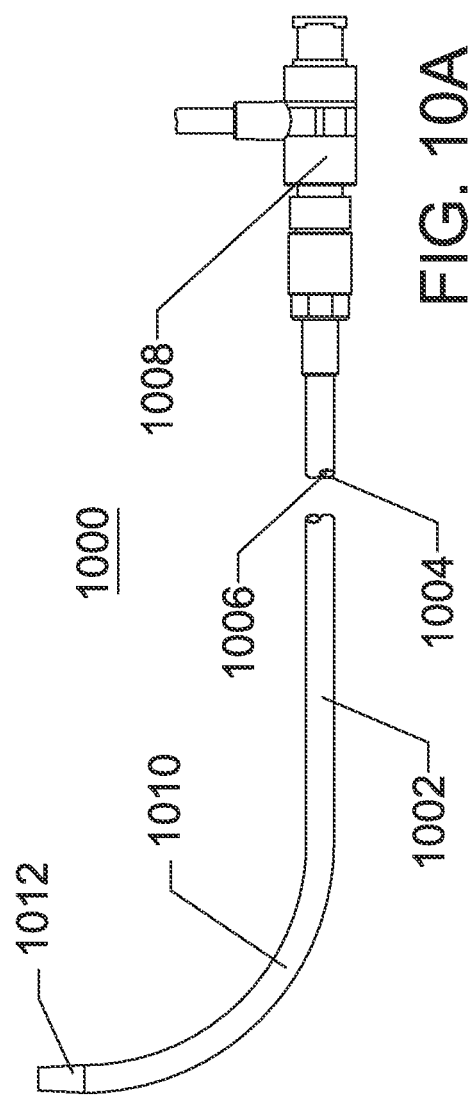
FIG. 10A illustrates an introducer comprising a sheath with a curved distal end.

FIG. 10A illustrates an introducer sheath 1000 comprising a tube 1002 further comprising a wall 1004, a lumen 1006, a sheath hub 1008 and a curved distal end 1010. The introducer sheath 1000 is preferably fabricated using reinforcing coils 1012 or braid (not shown) embedded within the wall 1004 to resist lumen collapse and also comprises a tapered exterior at its distal end to minimize any ridges or wall thickness where it tapers down over its dilator shaft 1030. The introducer sheath 1000 can further comprise one or more radiopaque markers 1014 (not shown) proximate the distal tip to facilitate imaging during use. The sheath wall 1004 can be configured to be substantially stiffer than the wall 1024 of the dilator 1020. The sheath 1000 wall 1004 can also be configured to be less stiff than the wall of the dilator 1020 to allow for the dilator 1020 to dominate the force balance between the two items, sheath 1000 and dilator 1020. The sheath wall 1004 can be configured with variable stiffness, for example with the proximal end being more stiff and resistant to bending than the distal portion of the sheath wall 1004.

The sheath hub 1008 can comprise a through-lumen, a locking proximal coupling, a sideport and line which can optionally be terminated with a stopcock. The sheath hub 1008 can further comprise a hemostasis valve, Tuohy-Borst valve, or the like (not illustrated).

The introducer sheath 1000 can comprise an inner diameter ranging from about 5 French to about 24 French or larger. A preferred inner diameter can range from about 7 French to about 14 French. The wall thickness of the introducer sheath 1000 can range from about 0.004 to about 0.013 inches. The overall length of the introducer sheath 1000, which includes the sheath hub 1008 determines the working length of the dilator 1020. The overall length of the dilator, which includes the dilator hub 1022, determines the working length of the steerable endoluminal punch 600. Materials of construction of the sheath 1000 and the dilator 1020 can include, but are not limited to, Pebax, Hytrel, polyurethane, PVC, PEEK, PE, HDPE, stainless steel, titanium nitinol, and the like.

The sheath 1000 tubing 1002 can comprise materials having hardness range of about 20 A to about 80 A with a preferred range of about 40 A to about 70 A. The hardness and wall configuration can be adjusted to provide a substantially resistance to bending and collapse. In the region of the curve 1010 the hardness and wall configuration should preferentially be adjusted to work with a substantially straight dilator such that when the dilator 1020 is removed, the sheath curve 1010 restores to a correct pre-set value such as about 20 degrees to about 180 degrees, with a preferred range of about 30 degrees to about 90 degrees (illustrated).

The sheath tubing wall 1004 can comprise braid reinforcement or coil reinforcement to facilitate bending but not tubing deformation or lumen 1006 collapse. The braid or coil reinforcement can comprise materials such as, but not limited to, polyester, stainless steel, nitinol, titanium, polyimide, and the like. The material can comprise a flat cross section or a rounded cross-section.

Figure 10B:
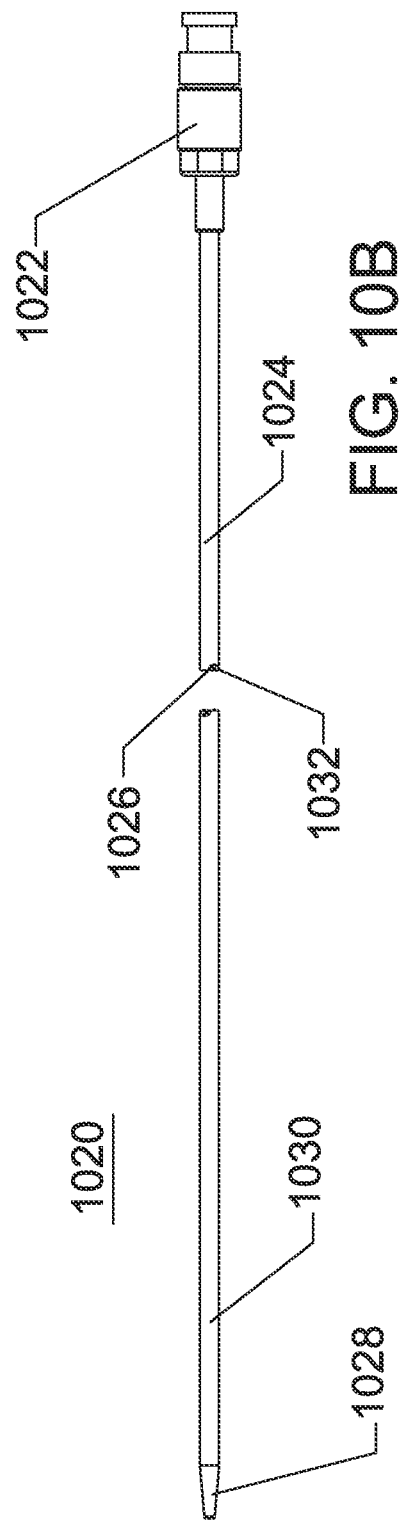
FIG. 10B illustrates a separate, substantially straight, removable dilator.

FIG. 10B illustrates a side view of a dilator 1020 comprising a substantially linear configuration with little or no lateral curvature in an unconstrained state. The dilator is preferably not pre-curved, but may take on a curved configuration when constrained by the sheath 1000 when translated through the lumen of the sheath, or forced to curve the sheath or endoluminal punch when those components are bent through operation by a surgeon during use. The dilator 1020 comprises a dilator hub 1022, and a tube 1024, further comprising a tube wall 1032, an internal lumen 1026, a straight distal end 1030, and a tapered distal end 1028. The wall stiffness of the dilator 1020 is optimized so that it can be easily articulated by a steerable endoluminal punch such as the one illustrated in FIG. 6, but is further capable of substantially reducing the curvature of the sheath 1000, when inserted therethrough. The dilator hub 1022 can comprise a proximal coupling mechanism, an optional hemostasis valve, Tuohy Borst valve. The dilator tubing 1024 can comprise a braid or coil reinforcement along at least a portion of its length or it can comprise unreinforced material.

Other aspects of the inventions include the method of use. In some embodiments, the patient's vasculature is accessed via a cutdown or a percutaneous procedure such as a Seldinger technique. After the percutaneous access port is placed, a guidewire is routed through the access port through the vasculature to the region near the target treatment site. The access port is removed and an introducer, comprising a dilator and sheath, is advanced over the guidewire to a region proximate the intended treatment site. In a preferred embodiment, the sheath 1000 comprises a distal end with curvature. The dilator 1020 comprises a distal end that is substantially straight. Both the sheath 1000 and dilator 1020 can comprise a degree of flexibility. The guidewire is next removed. A steerable endoluminal punch 600, with its blunt, protective stylet 900 locked in place and protruding out the distal end of the steerable endoluminal punch 600 is routed through a lumen of the dilator 1020 to a region proximate the distal end of the dilator 1020. The blunt, protective stylet 900 is next removed from the steerable endoluminal punch 600. The steerable endoluminal punch 600 is next articulated to form the desired curve and is aimed at the target region of tissue with a controlled degree of force, while still retracted inside the distal end of the dilator 1020. Once location is confirmed to be on target, the steerable endoluminal punch is advanced out the distal end of the dilator 1020, thus exposing the sharp tip of the punch 600 to tissue. The tip of the steerable endoluminal punch 600 cuts a hole, curved or arcuate incision or linear incision in the tissue. The steerable endoluminal punch 600 distal end, the tapered dilator and the sheath 1000 are next advanced through the incision in the tissue. A guidewire can be placed through the lumen of the steerable endoluminal punch or the lumen can be used for pressure measurement or dye injection.

In an embodiment, the lumen of the steerable endoluminal punch 600 can be about 0.023 inches in diameter with a preferred range of about 0.010 to 0.26 inches. The outside diameter of the inner tube of the steerable endoluminal punch 600 can be about 0.0355 to 0.0365 inches with a preferred range of about 0.032 to about 0.037 inches. The steerable endoluminal punch 600 and dilator 1020 can be removed from the sheath 1000 leaving the sheath, and optionally the guidewire if desired, in place. In other embodiments, the sheath 1000 is removed leaving only the guidewire in place to guide devices for follow-up procedures.

In the embodiment described above, the steerable endoluminal punch 600 controls the amount of curve of the dilator 1020 which can overwhelm and control the amount of curve of the sheath 1000. The dilator 1020, being substantially straight, is easily traversed by the substantially straight steerable endoluminal punch 600 with little or no tendency for the punch sharp distal end to shave material off the wall of the dilator or generate emboli. Once the dilator 1020 and steerable endoluminal punch 600 are removed, the sheath 1000 is free to assume its natural, curved state to facilitate follow-up procedures.

Figure 11:
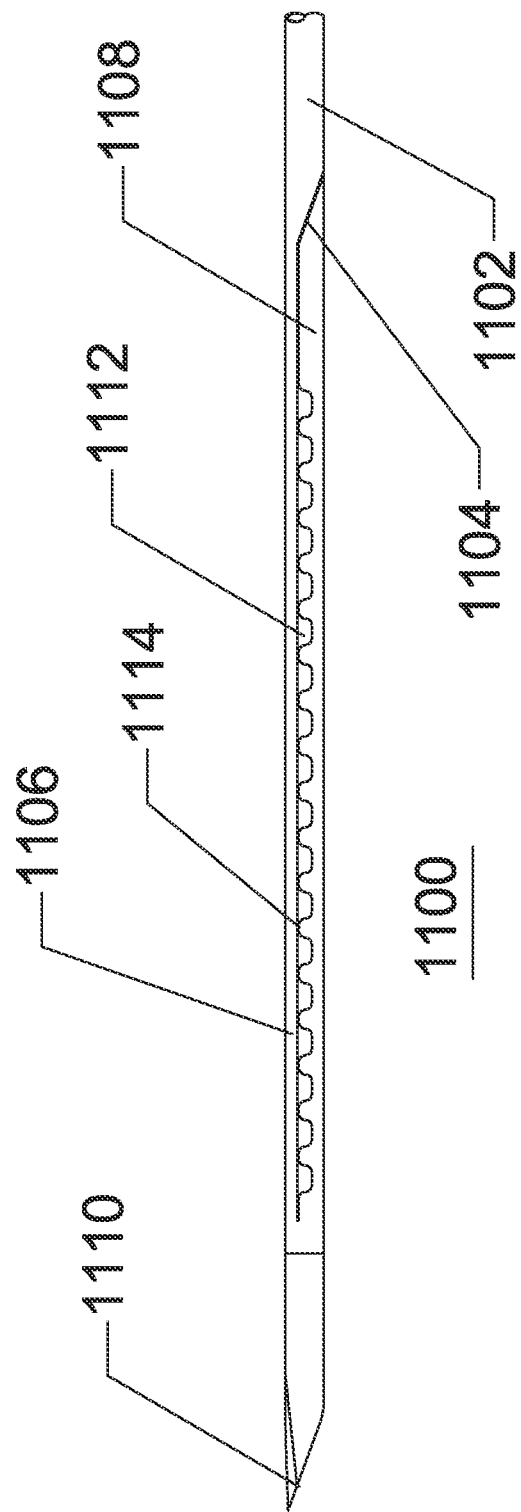
FIG. 11 illustrates an inner tube for a steerable endoluminal punch configured for increased flexibility.

FIG. 11 illustrates an inner tube 1100 configured for increased flexibility and in larger diameter sizes. The inner tube 1100 comprises longitudinal slot 1104 further modified with a plurality of cutouts 1112 to provide regions of additional flexibility in the inner tube 1100 while still maintaining a spacing function to hold the inner tube 1100 radially outward and adjacent to the inner wall of the outer tube 1200. The cutouts 1112 result in a structure that appears to resemble teeth from the side. It is beneficial to keep the longitudinal slot width minimized in the regions 1114 adjacent to and separating the cutouts 1112. The primary axis of the longitudinal slot 1104 can ride substantially centered when looking from the side, or it can ride off-axis, as illustrated. In FIG. 11, the primary axis of the slot 1104 rides higher than the central axis by about 0.011 inches but this distance can vary to achieve the appropriate area moment of inertia of the connected part 1106 and the separated part 1108. As the tube 1102 diameter grows, the area moment of inertia will likewise grow so steps need to be taken to reduce the area moment of inertia of the cross sections as well as preventing displacement or misalignment of the separated part 1108 from the connector part 1106. The distal tip 1110 of the inner tube 1100 is illustrated as being sharpened and is configured for use in generating an incision in tissue. Exemplary materials for construction of the inner tube include stainless steel such as 303, 304, 316 SS, and the like, precipitation hardening stainless steel, titanium, nitinol, and the like. The inner tube can also be fabricated from hard polymeric materials such as, but not limited to, PEEK, polyurethane, HDPE, high durometer Hytrel, Pebax, polyimides, and the like. The inner tube 1100 can be affixed to an anchor in the hub by means such as, but not limited to, adhesive, mechanical couplings such as pins, screws, and other fasteners, welding, soldering, and the like. The number of longitudinal slots 1104 can range between 1 and about 5, with a preferred arrangement including only a single slot separating a single element of material from the main control rod portion of the flexible region of the inner tube. The single slot, which appears a single slot from both sides of the tube, can be construed as a double slot coming together at a point in the sidewall of the tube. The resulting structure is a tube with a cutout that is not removed but is adherent to the tube at some point.

Figure 12:
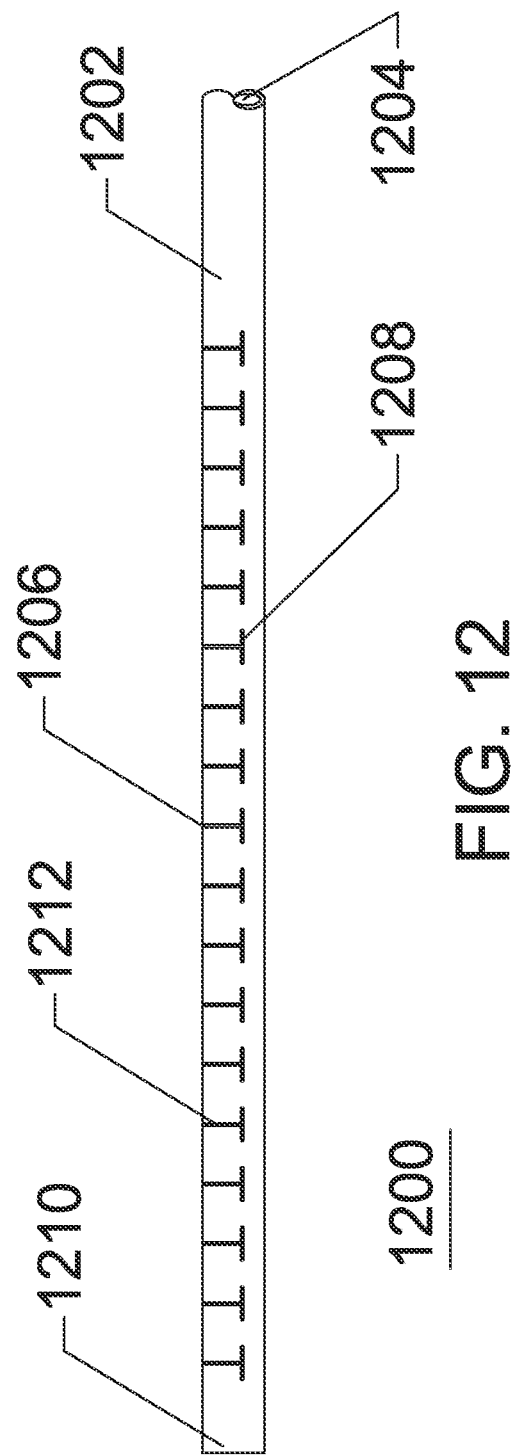
FIG. 12 illustrates an outer tube for a steerable endoluminal punch configured for increased flexibility.

FIG. 12 illustrates an outer tube 1200 configured for increased flexibility in larger diameter sizes. The outer tube 1200 comprises the tube wall 1202 and a central through-lumen 1204. The standard T (or H) slots 1212 in the outer tube 1200 are configured with the centerline of the longitudinal portion 1208 of the T or H slot 1202 to ride above or below the centerline of the tube. In the illustrated embodiment, the location of the longitudinal portion of the T or H slot 1206 is about 0.011 inches off axis but this location can vary with tubing diameter and wall thickness. The width of the connector slot 1206 of the T or H slot 1212 may be configured with additional opening width to permit more angular motion of the T or H slot 1212 when tensioned by the inner tube 1100. The width of the connector slot 1206 can vary between 0.001 inches and 0.020 inches with a preferred distance of about 0.002 to 0.004 inches to minimize the chance of yield in the material. Exemplary materials of construction for the outer tube 1200 include stainless steel, precipitation hardening stainless steel, titanium, nitinol, and the like. The inner tube 1100 can be affixed to an anchor in the hub by means such as, but not limited to, adhesive, mechanical coupling, welding, soldering, and the like.

Figure 13:
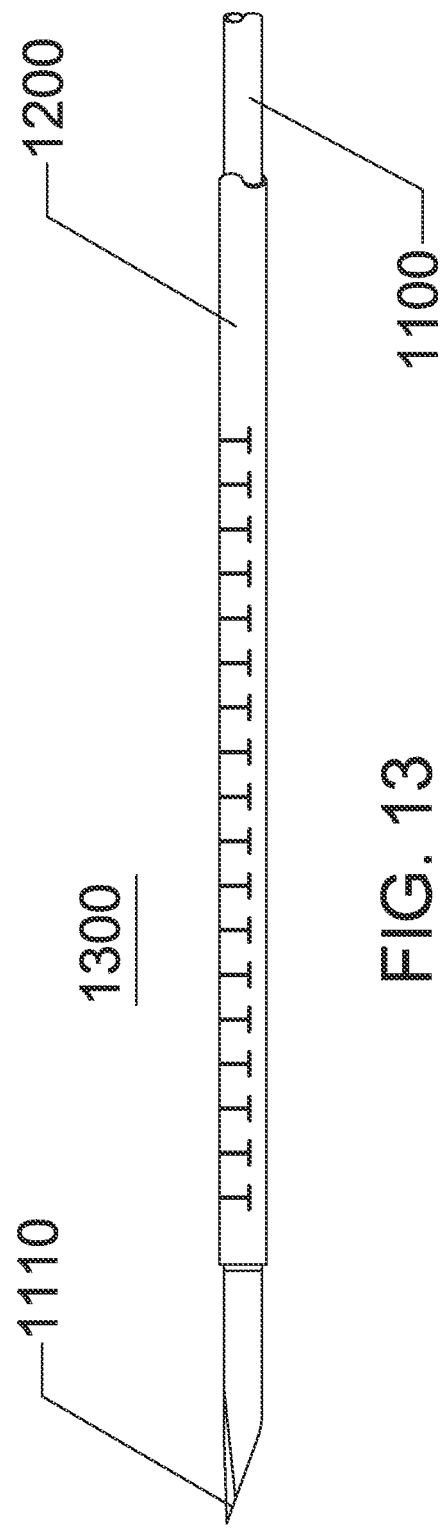
FIG. 13 illustrates an assembly of an inner tube and outer tube for a steerable endoluminal punch configured for increased flexibility.

FIG. 13 illustrates an assembly 1300 of the inner tube 1100 of FIG. 11 with the outer tube 1200 of FIG. 12 to result in a steerable endoluminal punch of increased flexibility. The cutouts 1112 are preferably aligned with the T or H slots 1212 to facilitate bending in the region of the longitudinal portion 1208 of the T or H slots 1212. The illustrated configuration shows a 15 gauge outer tube and a 17 gauge inner tube. This configuration is larger in diameter than 18 gauge devices. The increased diameter of the inner tube 1100 facilitates increased off-axis moment arm and increased bending force being imparted on the inner tube. However, the area moment of inertia of this larger system is greater than that of the smaller diameter devices and so increasing flexibility may be beneficial in exercising control. This larger diameter 15 gauge system comprises a center lumen 1108 through the inner tube 1100 that can slidably pass a 0.035 or 0.038 guidewire or a center punch with a diameter up to about 0.045 inches or greater. The hub system of the steerable endoluminal punch tubing assembly 1300 of FIG. 13 can be the same as that of smaller diameter devices, except for provision for mating with larger diameter tubes.

The steerable endoluminal punch of FIG. 13 can further be configured, in other embodiments, with a blunt distal end 1110 on the inner tube 1200, rather than the sharp distal end 1110 as illustrated. In the blunt distal end configuration, the inner tube and outer tube can be combined to form a device that is a steerable introducer or catheter and is not necessarily a punch.

Figure 14A:
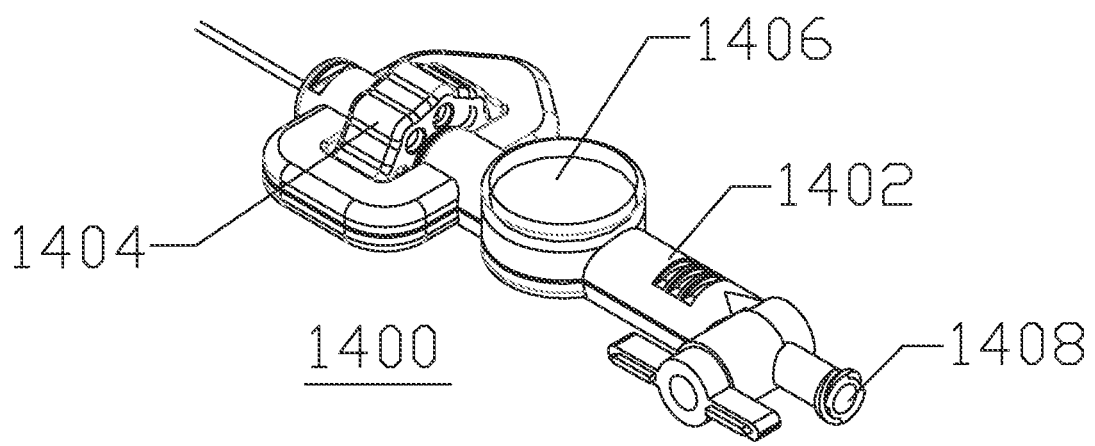
FIG. 14A illustrates an oblique view of a proximal hub assembly for a steerable endoluminal punch further comprising a gauge configured to display the amount of bending control applied to the tip through the hub.
Figure 14B:
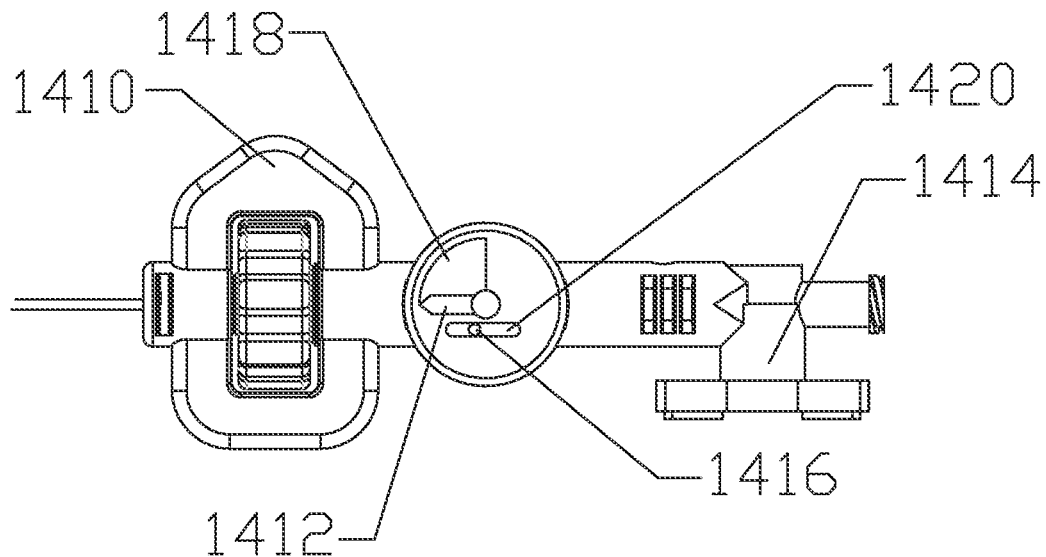
FIG. 14B illustrates a top view of the proximal hub assembly for the steerable endoluminal punch further comprising the gauge.
Figure 14C:
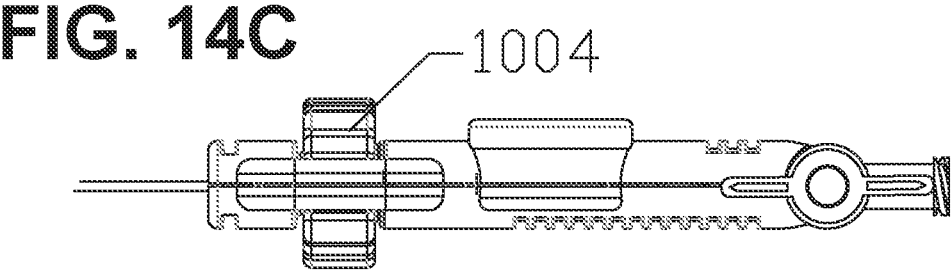
FIG. 14C illustrates a side view of the proximal hub assembly for the steerable endoluminal punch.

FIG. 14 illustrates the hub 1400 of a steerable endoluminal punch. The hub 1400 further comprises a hub body 1402, a control knob 1404, a deflection gauge 1406 further comprising a linkage 1416, an optional calibration marking or range of motion display 1418, and a gauge pointer 1412, a through-lumen 1408, a pointer flange 1410, and a stopcock 1414. The hub 1400 is configured with the gauge to allow the user to see exactly how much deflection force is being imposed on the distal tip and in which direction that the tip is being deflected. This information is very useful for the user when negotiating tortuous anatomy.

The deflection gauge, in the illustrated embodiment, operates off of a direct linkage 1416 to a moving element within the hub, in this case, the jackscrew traveler (not shown). The direct linkage 1416 rotates the gauge pointer 1412 by means of a slot 1420 in the gauge pointer 1412. The deflection gauge could also be a digital readout, an analog electrical readout, or the like. The deflection gauge can be driven by means of a direct linkage, as shown, or by strain gauges affixed to the device either in the hub or in the tubing.

Figure 15A:
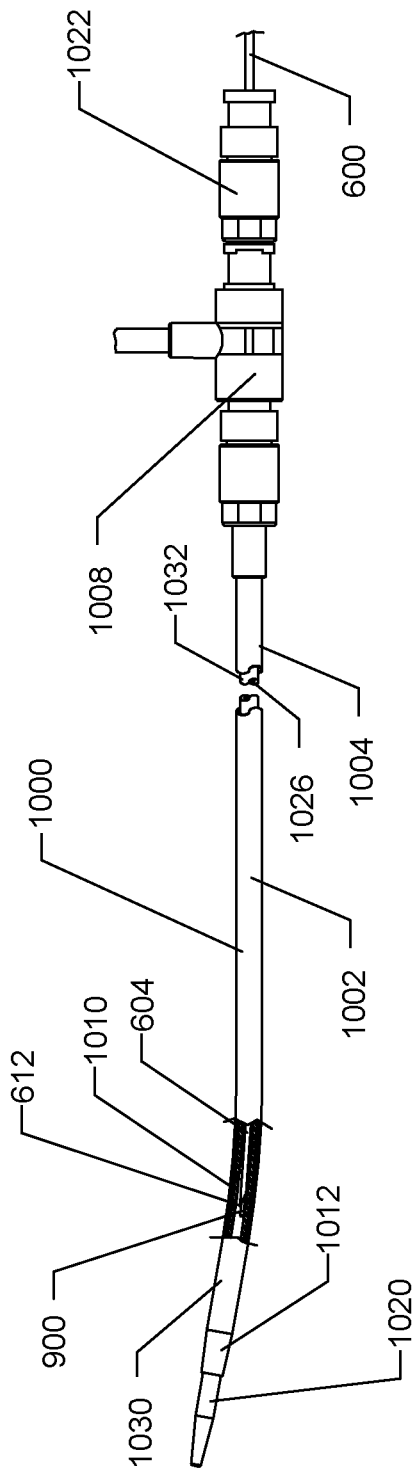
FIG. 15A illustrates the tip of the steerable endoluminal punch being advanced through the distal curved section of a dilator lumen, previously placed within the lumen of a sheath, wherein the sharp tip is being shielded from the dilator wall by a short, blunt stylet protruding distally to the sharp tip.
Figure 15B:
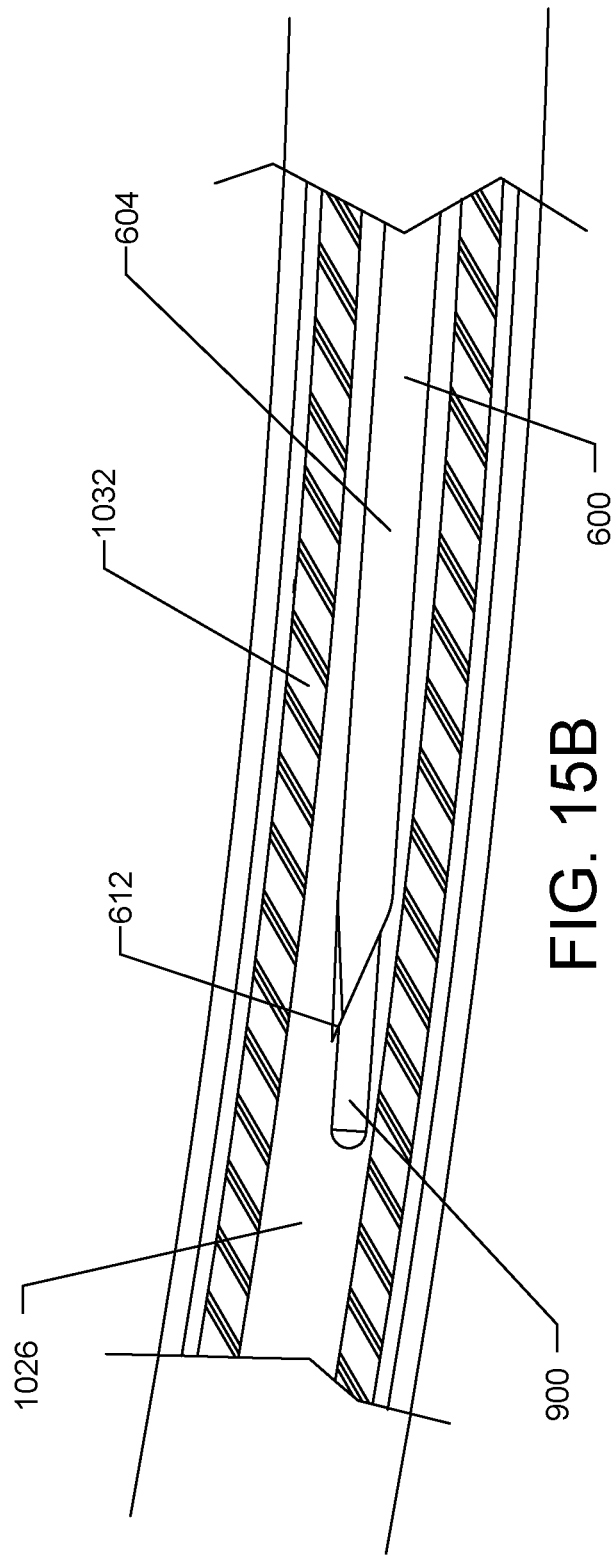
FIG. 15B illustrates an enlargement of the breakaway section in the curved region of FIG. 15A.

FIG. 15A illustrates a side view in partial cross-section of the introducer system of FIG. 10 wherein a steerable needle or punch (steerable endoluminal punch) 600 has been inserted into the central lumen of the pre-placed dilator 1020 within the sheath 1000. FIG. 15B illustrates an enlarged view of the cutaway section in the curvature region of FIG. 15A. The curvature at the distal end 1010 of the sheath 1000 is substantially straightened out by the presence of the dilator 1020, thus affording a substantially straight dilator lumen 1026 when it gets to the distal region 1030. This mostly straightened out dilator lumen 1026 permits the punch tip 612 to be advanced through the curved distal end of the sheath 1000 with a reduced tendency to scrape the dilator walls 1032 and skive off plastic materials into the lumen 1026. The presence of a large diameter, blunted stylet 900 pre-placed within the steerable endoluminal punch 600, shields the sharp tip 612 of the steerable endoluminal punch from the dilator wall 1032 even should the steerable endoluminal punch 600 encounter higher degrees of curvature in the sheath tubing 1002 or dilator tubing 1032. This shielding by the blunted stylet 900 helps preserve tip 612 sharpness and, again, reduces the risk of plastic skiving. The blunt stylet 900 tip is beneficially large in diameter relative to the lumen through which it is passed so that it minimizes the radial distance between the stylet 900 outside diameter and the inside diameter of the steerable endoluminal punch 600. The blunt stylet 900 tip can comprise a hemispherical, rounded, or mushroom configuration, for example. The blunt stylet tip can be larger in diameter than the stylet shaft to which it is affixed, thus reducing insertion friction through the steerable endoluminal punch lumen. For example, the stylet shaft can comprise a wire or tube with an outside diameter of about 0.016 to 0.018 inches while the blunt stylet tip 900 can be a segment of metal tubing which is welded to the shaft wire or tube. The distal end of the blunt stylet 900 tip can be formed round using adhesives, metal forming, melting such as using a laser beam or other heat source, or the like. The metal stylet 900 tip can also be rounded using standard machining or grinding techniques. The blunt stylet tip 900 can, in another embodiment, comprise a hollow configuration with expandable struts which permit its diameter to be spring biased open more than the inside diameter of the steerable endoluminal punch 600 and thus provide additional shielding for the sharp tip 612. The expandable struts can be fashioned as longitudinally oriented leaf springs, for example, but other expandable configurations such as those found in many cardiovascular and intraluminal stents would also work.

The steerable endoluminal punch 600 is capable of now articulating or deflecting the distal end of the composite system by means of controls on the hub of the steerable endoluminal punch 600 or through external control using robotics artificial intelligence, human control, or the like. The steerable endoluminal punch 600 and dilator 1020 can next be removed from the lumen 1006 of the sheath 1000 to permit introduction of other instruments for therapy or diagnosis by way of the sheath 1000.

FIG. 16A illustrates an introducer system 1600 for use with the steerable endoluminal punch. The introducer system 1600 comprises an axially elongate sheath 1602 defined by a proximal and a distal end, further comprising a sheath wall 1604 and a central through-lumen and an obturator or dilator 1610. The dilator 1620 comprises a tapered distal tip 1628 and at least one lumen 1626 configured to accept guidewires, permit fluid passage, slidably pass the steerable endoluminal punch, and the like. The introducer 1600 further comprises an expandable enlargement 1612 affixed or integral to the exterior of the dilator tube. The expandable enlargement 1612 is preferably located on the distal end of the dilator, proximal to the tapered distal tip of the sheath/ dilator system. The expandable enlargement 1612 can be configured to project outward radially through one or more windows 1618 or fenestrations cut into the wall 1604 of the sheath. The expandable enlargement 1612 can be provided enlarged or it can be configured to be controllably enlarged by an action by the user or some controller. In the illustrated embodiment, a control lever 1634 is operably connected to the dilator hub 1614 and moves a control wire or rod 1636. The expandable enlargement 1612 can also be configured to reduce in diameter or retract completely within the exterior profile of the sheath wall 1604. The expandable enlargement 1612 can comprise structures, such as but not limited to, a moly-bolt expandable section, a wire loop, expandable balloons, and the like. Radial enlargement of the structure 1612 can occur, due to pressurization or inflation by means of a fluid port on the proximal end and a fluid channel leading to a balloon or other expandable structure. Radial enlargement can also occur due to the relative motion of an inner and outer portion of the sheath that causes the moly-bolt structure to bend wider or straighten narrower. Radial enlargement can also occur due to a wire or control rod 1636 (illustrated) that is advanced or retracted to form one or more loops or petals or otherwise actuate the expansion mechanism (a moly bolt expansion mechanism is illustrated). Radial enlargement can also be generated by electrical actuation (heating, etc.) of a nitinol element pre-treated to expand to a larger diameter. This enlarged portion of the sheath is configured to prevent the sheath from passing too far into the left atrium of the heart or other structure during advancement and tissue puncture. Radial enlargement of elements 1612 can also be generated by longitudinal or rotational movement of the dilator relative to the introducer sheath.

The endoluminal punch system can be combined with robotic controllers to create robotic cardiac access system. An introducer sheath and dilator 1706, a steerable endoluminal punch 1708 can be controlled with a robotic system when combined with a position reference or registration between the patient 1702 and the steerable endoluminal punch. The position reference 1710 can comprise a reference to the patient 1702 directly, including registrations marks or markers, anatomical landmarks, and the surgical table or a reference to the floor 1712, which is positioned relative to the surgical table, which is positioned relative to the patient. The position reference may be affixed to the steerable endoluminal punch either directly or through intermediate linkages, actuators, or the like.

In such a system, one or more linear or rotational actuators may be affixed to the steerable endoluminal punch, introducer sheath and dilator, and/or other diagnostic or therapeutic instrument to provide for axial movement, rotational movement, and deflection in at least one plane substantially orthogonal to the longitudinal axis of the steerable endoluminal punch or other instrument. For example, the linear or rotational actuators may be affixed to the position reference. The linear or rotational actuators can be controlled, in whole or in part, by inputs directly from the user. The linear or rotational actuators can also be controlled, in whole or in part, by a computer system employing position feedback, artificial intelligence, rule-based logic, or the like.

In some embodiments, the control knob mechanism on the hub can be replaced by a gear or other linkage leading to a controller. A transmission system can be beneficially added to the system to provide for mechanical advantage. The controller can comprise a stepper motor, brushless dc motor, a standard brushed motor, pneumatic actuator, linear actuator, hydraulic actuator, or the like. The controller system can include a power supply such as a battery, a wiring bus, control electronics, and any associated power supply electronic components. The controller can be operatively connected to a control switch or dial, or it can be connected to a computer system, either onboard or remote from the steerable endoluminal punch. The controller can be connected to a computer by methodology such as, but not limited to, wiring bus, Wi-fi, Bluetooth or other RF protocols, ultrasound, microwave, optical transmission, and the like. The computer can include devices such as, mainframes, laptops, tablet computers, cell phones, and the like. Thus, this system can be easily optimized for use in robotic surgery, robotic endovascular therapy, and the like. Monitoring of performance and position can be conducted by means such as, but not limited to, ultrasound, fluoroscopy, electromagnetic mapping, GPS positioning, and the like. Movement of the patient or even a target organ in the patient can be referenced to the location of the object to which the steerable endoluminal punch is affixed by way of radiopaque markers and a fluoroscope (single or biplanar), a simple physical marker on the patient and cameras.

The hub of the dilator, the hub of the sheath, and the hub of the steerable endoluminal punch can be grasped by stabilizers, clamps, linear or rotational actuators, or other systems that permit stabilization and controlled movement. The stabilizers can be affixed or grounded relative to the cath lab walls, ceilings or floors, the operating table, the patient, or other reference points. Movement of each of these segments can be controlled in the axial and rotational directions. The hub can comprise controls such as those which adjust tip curvature and these control mechanisms, such as a control knob or gearbox, can be moved in a controllable fashion to generate robotic access to the patient in a transvascular capacity. An axial linear stage can be used to advance or retract the steerable endoluminal punch and any concomitant introducers, catheters, etc. The distal tip of the steerable endoluminal punch can be deflected in two orthogonal directions by means disclosed in U.S. Pat. No. 9,993,266 using orthogonally displaced internal control rods and keepers. Each direction can be separately actuated by controls at the proximal end of the steerable endoluminal punch.

The hub can be grasped by an actuator with the ability to rotate the hub about its axis, advance or retract the hub (distally or proximally respectively), or dial in a specific amount of lateral tip deflection. The actuator can be in the form of a robotic arm, a stabilizer and clamp powered by electrical motors, stepper motors, pneumatic or hydraulic actuators, linear actuators, or the like. The actuator system can also control injection or withdrawal of fluids through the central lumen of the steerable endoluminal punch as well as controlling the advancement and orientation of a guidewire or other central device. By the systems enclosed herein, a steerable endoluminal punch, with or without a compatible introducer or catheter, can be introduced into a patient and robotically driven to any spot in the body, whether through vasculature or through tissue such as muscle, fat, organs, and the like. Provision can be made to allow for physician go-ahead or override at various points in the procedure.

The present invention may be embodied in other specific forms without departing from its spirit or essential characteristics. The described embodiments are to be considered in all respects only as illustrative and not restrictive. For example, the tip of the steerable endoluminal punch can be rounded and blunt with a slit in the center. A cutter can be actuated, from the proximal end, for example, to project out beyond the round tip, to perform a slice while keeping the steerable endoluminal punch dull and unlikely to puncture tissue or skive plastic off the inside of a dilator. The blade pushed out through the linear groove in the blunt tip can be operably connected to a linkage to provide reciprocating, side-to-side motion and cut a slit in the tissue that is wider than the diameter of the steerable endoluminal punch. Control over forces applied to the hub, including relative force application to the inner and outer tubes and control rods and rotation of the system about its longitudinal axis can be controlled by electromechanical actuators and computerized controllers, or the like. The cutting element on the introducer dilator can be operably connected to a vibratory transducer, operating in the range of about 0.1 Hz to about 50 kHz (well into the ultrasonic range), by way of a linkage from the transducer to the cutting blade, to provide for energy delivery to facilitate cutting of scarred or difficult to penetrate tissue. In yet other embodiments, the tip of the endoluminal punch can be configured to create an arc shaped slit, rather than a punch hole, wherein the total length of the arc is greater than the width of the tip of the endoluminal punch, thus allowing easier tissue penetration than if a simple hole were punched in the tissue and then expanded. A slit in tissue has higher stresses at its ends, when expanded, thus permitting easier incision and passage of instrumentation through the hole than would be permitted with the dilated hole.

We claim:

1. An endoluminal punch system comprising:
    an axially elongate sheath having a distal end and a proximal end, and a lumen extending from said proximal end to said distal end,
    a dilator further comprising a tube having a proximal end, a distal end, a tapered dilator tip at said distal end, and a dilator lumen extending therethrough, said dilator slidably disposed within the lumen of the sheath to position the tapered dilator tip to extend distally from the distal end of the sheath;
    an endoluminal punch slidably disposed within the dilator, said endoluminal punch having a distal end configured to penetrate tissue;
    wherein the dilator lumen is configured to accommodate passage of the endoluminal punch;
    an electrode suitable for emission of radiofrequency energy or microwave energy, said electrode disposed proximate the distal end of the dilator.

2. The endoluminal punch system of claim 1, wherein: the electrode comprises a ring electrode affixed to the distal tip of the dilator.

3. The endoluminal punch system of claim 1, wherein: the electrode comprises a linear electrode affixed to the distal tip of the dilator.

4. The endoluminal punch system of claim 1, further comprising:
    a radiofrequency generator configured to deliver radiofrequency energy in the range of about 2 to about 20 Watts with a preferred range of about 5 to about 15 Watts.

5. The endoluminal punch system of claim 1 further comprising an expandable structure disposed proximate the distal end of the dilator, to prevent excessive penetration of the endoluminal punch system through tissue.

6. The endoluminal punch system of claim 1 further comprising a mechanism to stabilize the system relative to anatomical landmarks in a patient.

7. A method of penetrating tissue, comprising the steps of:
    providing an endoluminal punch system comprising:
    an axially elongate sheath having a distal end and a proximal end, and a lumen extending from said proximal end to said distal end,
    a dilator further comprising a tube having a proximal end, a distal end, a tapered dilator tip at said distal end, and a dilator lumen extending therethrough, said dilator slidably disposed within the lumen of the sheath to position the tapered dilator tip to extend distally from the distal end of the sheath;
    an endoluminal punch slidably disposed within the dilator, said endoluminal punch having a distal end configured to penetrate tissue;
    wherein the dilator lumen is configured to accommodate passage of the endoluminal punch;
    an electrode suitable for emission of radiofrequency energy, said electrode disposed proximate the distal end of the dilator;
    advancing the endoluminal punch system to place the tapered dilator tip and surrounding sheath against the tissue;
    holding the tapered dilator tip and distal end of the sheath against the tissue;
    advancing the distal end of the punch distally into the dilator tip to perforate the tissue;
    energizing the electrode with radiofrequency energy to create or enlarge a hole in the tissue to permit advancement of the dilator tip through the tissue; and
    advancing the dilator tip through tissue.

8. The method of claim 7, further comprising the step of retracting the punch proximally into the tapered distal tip of the dilator before performing the step of advancing the dilator tip through tissue.

9. The method of claim 7, wherein the step of energizing the electrode comprising delivering radiofrequency energy in the range of about 2 to about 20 Watts with a preferred range of about 5 to about 15 Watts to the electrode.

10. A method of penetrating tissue, comprising the steps of:
    providing an endoluminal punch system comprising:
    an axially elongate sheath having a distal end and a proximal end, and a lumen extending from said proximal end to said distal end,
    a dilator further comprising a tube having a proximal end, a distal end, a tapered dilator tip at said distal end, and a dilator lumen extending therethrough, said dilator slidably disposed within the lumen of the sheath to position the tapered dilator tip to extend distally from the distal end of the sheath;
    an endoluminal punch slidably disposed within the dilator, said endoluminal punch having a distal end configured to penetrate tissue;
    wherein the dilator lumen is configured to accommodate passage of the endoluminal punch; and
    an electrode suitable for emission of ohmic heating, said electrode disposed proximate the distal end of the dilator;
    advancing the endoluminal punch system to place the tapered dilator tip and surrounding sheath against the tissue;
    holding the tapered dilator tip and distal end of the sheath against the tissue;
    advancing the distal end of the punch distally into the dilator tip to perforate the tissue;
    energizing the electrode with ohmic heating to create or enlarge a hole in the tissue to permit advancement of the dilator tip through the tissue; and
    advancing the dilator tip through tissue.

11. The method of claim 10, further comprising the step of retracting the punch proximally into the tapered distal tip of the dilator before performing the step of advancing the dilator tip through tissue.

12. The method of claim 10, wherein the step of energizing the electrode comprising delivering radiofrequency energy in the range of about 2 to about 20 Watts with a preferred range of about 5 to about 15 Watts to the electrode.

\* \* \* \* \*